(12) United States Patent
Bubendorf et al.

(10) Patent No.: US 8,039,473 B2
(45) Date of Patent: Oct. 18, 2011

(54) SOLID FORMS OF [4-(3-FLUORO-5-TRIFLUOROMETHYL-PYRIDIN-2-YL)-PIPERAZIN-1-YL-[5-METHANESULFONYL-2-((S)-2,2,2-TRIFLUORO-1-METHYL-ETHOXY)-PHENYL]-METHANONE

(75) Inventors: Andre Bubendorf, Uffheim (FR); Annette Deynet-Vucenovic, Loerrach (DE); Ralph Diodone, Breisach (DE); Olaf Grassmann, Loerrach (DE); Kai Lindenstruth, Loerrach (DE); Emmanuel Pinard, Linsdorf (FR); Franziska E. Rohrer, Riehen (CH); Urs Schwitter, Reinach BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/841,195

(22) Filed: Jul. 22, 2010

(65) Prior Publication Data

US 2010/0311971 A1    Dec. 9, 2010

Related U.S. Application Data

(63) Continuation of application No. 12/002,997, filed on Dec. 19, 2007, now abandoned.

(30) Foreign Application Priority Data

Dec. 28, 2006    (EP) .................................... 06127269

(51) Int. Cl.
*A61K 31/496*    (2006.01)
*C07D 213/74*    (2006.01)

(52) U.S. Cl. .................................. 514/253.01; 544/360
(58) Field of Classification Search ...................... None
See application file for complete search history.

(56) References Cited

U.S. PATENT DOCUMENTS

2008/0214561 A1    9/2008    Bubendorf et al.

FOREIGN PATENT DOCUMENTS

| WO | 2004/071486 | * | 8/2004 |
| WO | 2004071486 |   | 8/2004 |
| WO | 2005/014563 | * | 2/2005 |

OTHER PUBLICATIONS

Hancock et al. Pharm. Res. 17(4), pp. 397-404 (2000).*
International Search Report issued Apr. 8, 2008 in corresponding PCT/EP2007/064104.
Translation of Chinese Office Action dated May 24, 2011.

* cited by examiner

*Primary Examiner* — Emily Bernhardt
(74) *Attorney, Agent, or Firm* — George W. Johnston; Patricia S. Rocha-Tramaloni; Kimberly J. Prior

(57) ABSTRACT

The present invention relates to four distinct crystalline forms and to an amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone, and to their use in the preparation of pharmaceutical compositions. The compounds of present invention are suitable for the treatment of psychoses, pain, neurodegenerative disfunction in memory and learning, schizophrenia, dementia and other diseases in which cognitive processes are impaired, such as attention deficit disorders or Alzheimer's disease.

13 Claims, 21 Drawing Sheets

SOLID FORMS OF [4-(3-FLUORO-5-TRIFLUOROMETHYL-PYRIDIN-2-YL)-PIPERAZIN-1-YL-[5-METHANESULFONYL-2-((S)-2,2,2-TRIFLUORO-1-METHYL-ETHOXY)-PHENYL]-METHANONE

PRIORITY TO RELATED APPLICATION(S)

This application is a continuation of U.S. application Ser. No. 12/002,997, filed Dec. 19, 2007, now pending; which claims the benefit of European Patent Application No. 06127269.6 filed Dec. 28, 2006. The entire contents of the above-identified applications are hereby incorporated by reference.

BACKGROUND OF THE INVENTION

[4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone has been already described in published PCT patent application No. WO 2005/014563.

SUMMARY OF THE INVENTION

The present invention provides four distinct crystalline forms and to an amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone, and to their use in the preparation of pharmaceutical compositions.

The four distinct crystalline forms and amorphous form of 4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone are suitable for preparing a pharmaceutical formulation.

In a first aspect, the present invention relates to three distinct crystalline forms A, B and C of the following compound:

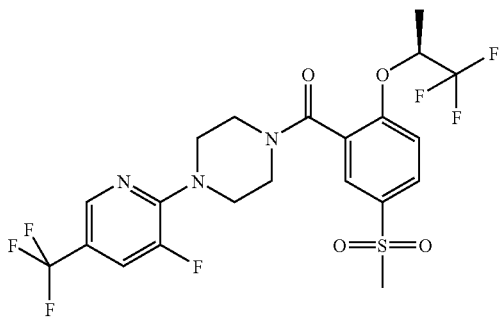

In another aspect, the present invention relates to the amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

In another aspect, the present invention relates to a methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

In a further aspect, the invention relates to a pharmaceutical composition comprising a crystalline form A, B, C or an amorphous form or a methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone as an active ingredient.

In still a further aspect, the invention relates to a method for the treatment of treating psychoses, pain, neurodegenerative disfunction in memory and learning, schizophrenia, dementia and other diseases in which cognitive processes are impaired, such as attention deficit disorders or Alzheimer's disease which comprises administering a therapeutically effective amount of a crystalline form A, B, C or an amorphous form or a methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

The aforementioned solid forms can be distinguished by physical and chemical properties that can be characterized by infra-red spectra, X-ray powder diffraction patterns, melting behavior or glass transition temperatures.

DETAILED DESCRIPTION OF THE INVENTION

Figure 1:
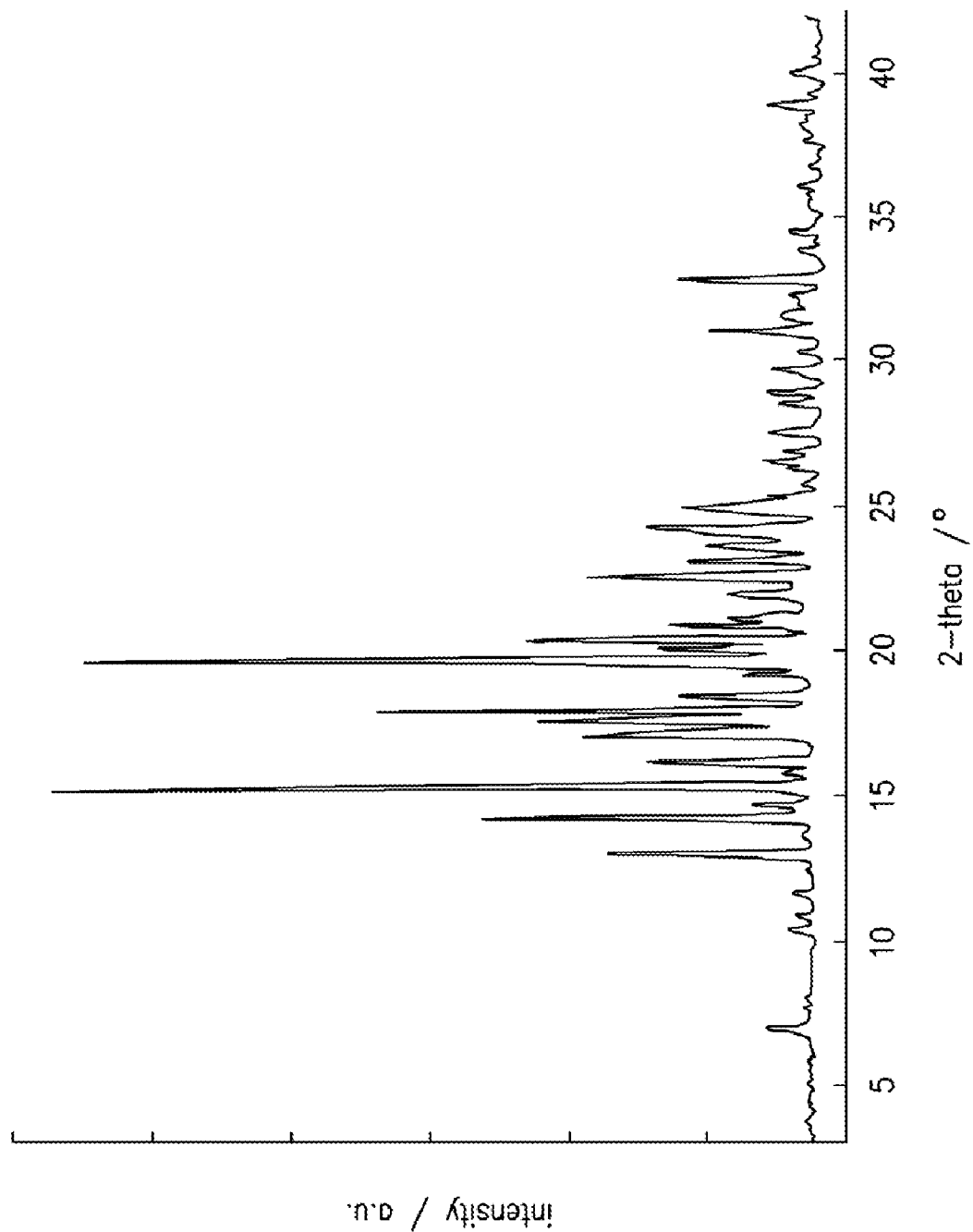
FIG. 1: shows a XRPD (Powder X-Ray Powder Diffraction) pattern of a typical lot of form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

As used herein, "amorphous forms" or "amorphous" denotes a material that lacks long range order and as such does not show sharp X-ray peaks, i.e. a Bragg diffraction peak. The XRPD pattern of an amorphous material is characterized by one or more amorphous halos.

Bragg's law describes the diffraction of crystalline material with the equation:

$$2d \sin\theta = n\lambda$$

wherein d=perpendicular distance between pairs of adjacent planes in a crystal (d-spacing), theta=Bragg angle, lambda=wavelength and n=integer.

When Bragg's law is fulfilled, the reflected beams are in phase and interfere constructively so that Bragg diffraction peaks are observed in the X-ray diffraction pattern. At angles of incidence other than the Bragg angle, reflected beams are out of phase and destructive interference or cancellation occurs. Amorphous material does not satisfy Bragg's law and no Bragg diffraction peaks are observed in the X-ray diffraction pattern.

"An amorphous halo" is an approximately bell-shaped diffraction maximum in the X-ray powder diffraction pattern of an amorphous substance. The FWHM of an amorphous halo is bigger than two degrees in 2-theta.

"FWHM" means full width at half maximum, which is a width of a peak appearing in an XRPD pattern at its half height.

"API" is used herein as an acronym of Active Pharmaceutical Ingredient.

"DSC" is used herein as an acronym of Differential Scanning Calorimetry. DSC curves were recorded using a Mettler-Toledo™ differential scanning calorimeter DSC820 or DSC 821 with a FRS05 sensor. System suitability tests and calibrations were carried out according to the internal standard operation procedure.

For the measurements of crystalline forms approximately 2-6 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 100 mL/min using heating rates of 10 K/min.

For the measurements of amorphous forms, approximately 2-6 mg of sample were placed in aluminum pans, accurately weighed and hermetically closed. The samples were then heated under a flow of nitrogen of about 100 mL/min using heating rates of 10 K/min.

"DVS" is used herein as an acronym of Dynamic Vapor Sorption. DVS isotherms were collected on a DVS-1 (SMS Surface Measurements Systems) moisture balance system. The sorption/desorption isotherms were measured stepwise in a range of 0% RH to 90% RH at 25° C. A weight change of <0.002 mg/min was chosen as criterion to switch to the next level of relative humidity (with a maximum equilibration time of six hours, if the weight criterion was not met). The data were corrected for the initial moisture content of the samples; that is, the weight after drying the sample at 0% relative humidity was taken as the zero point.

"Form A" is used herein as abbreviation for the crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

"Form B" is used herein as abbreviation for the crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

"Form C" is used herein as abbreviation for the crystalline form C of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

"Methylparaben cocrystal form" is used herein as abbreviation for the methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

"IR" is used herein as an acronym of Infra Red, hence "IR spectrum" means Infra Red Spectrum. The IR-spectrum of the sample was recorded as film of a Nujol suspension consisting of approx. 5 mg of sample and few Nujol between two sodium chloride plates, with an FT-IR spectrometer in transmittance. The Spectrometer was a Nicolet™ 20SXB or equivalent (resolution: 2 $cm^{-1}$, 32 or more coadded scans, MCT detector).

"XRPD" is used herein as an acronym of X-Ray Powder Diffraction. X-ray diffraction patterns were recorded at ambient conditions in transmission geometry with a STOE STADI P diffractometer (Cu Kα radiation, primary monochromator, position sensitive detector, angular range 3 to 42 2Theta (deg), approximately 60 minutes total measurement time).

The samples were prepared and analyzed without further processing (e.g. grinding or sieving) of the substance.

Alternatively, X-ray diffraction patterns were recorded in transmission geometry with a STOE STADIP diffractometer with CuKα radiation (1.54 Å) and a position sensitive detector. The samples (approximately 50 mg) were prepared between thin polymer (or aluminum) films and analyzed without further processing (e.g. grinding or sieving) of the substance.

X-ray diffraction patterns were also measured on a Scintag X1 powder X-ray diffractometer equipped with a sealed copper Kα 1 radiation source. The samples were scanned from 2 to 36 2Theta (deg) at a rate of 1 degree 2Theta per minute with incident beam slit widths of 2 and 4 mm and diffracted beam slit widths of 0.3 and 0.2 mm.

For single crystal structure analysis a single crystal was mounted in a loop on a goniometer and measured at ambient conditions. Alternatively, the crystal was cooled in a nitrogen stream during measurement. Data were collected on a STOE Imaging Plate Diffraction System (IPDS) from STOE (Darmstadt). In this case Mo-radiation of 0.71 Å wavelength was used for data collection. Data was processed with STOE IPDS-software. The crystal structure was solved and refined with standard crystallographic software. In this case the program ShelXTL from Bruker AXS (Karlsruhe) was used.

Alternatively, for synchrotron radiation was used for data collection. A single crystal was mounted in a loop and cooled to approximately 100 K in a nitrogen stream. Data was collected at the Swiss Light Source beamline X10SA using a MAR CCD225 detector with synchrotron radiation and data processed with the program XDS. The crystal structure was solved and refined with standard crystallographic software. In this case the program ShelXTL from Bruker AXS (Karlsruhe) was used. The crystal structure was solved and refined with ShelXTL (Bruker AXS, Karlsruhe)

"TGA" is used herein as an acronym of Thermo Gravimetric Analysis. TGA curves were measured on a Mettler-Toledo™ thermogravimetric analyzer (TGA850 or TGA851). System suitability tests and calibrations were carried out according to the internal standard operation procedure.

For the thermogravimetric analyses, approx. 5 to 10 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 50 mL/min using a heating rate of 5 K/min.

"Pharmaceutically acceptable" such as pharmaceutically acceptable carrier, excipient, adjuvant, preservatives, solubilizers, stabilizers, wetting agents, emulsifiers, sweeteners, colorants, flavoring agents, salts for varying the osmotic pressure, buffers, masking agents or antioxidants, etc., means pharmacologically acceptable and substantially non-toxic to the subject to which the particular compound is administered.

"Pharmaceutically acceptable" hence means substantially non-toxic to the subject to which the pharmaceutically acceptable material is administered.

A "cocrystal" is formed between a molecular or ionic API and a cocrystal former that is a solid under ambient conditions, i.e. a cocrystal is a multi-component crystalline material comprising two or more solids (at ambient conditions).

"Therapeutically effective amount" means an amount that is effective to prevent, alleviate or ameliorate symptoms of disease or prolong the survival of the subject being treated.

As already mentioned hereinabove, the present invention relates to four novel crystalline forms and to an amorphous form of the following compound:

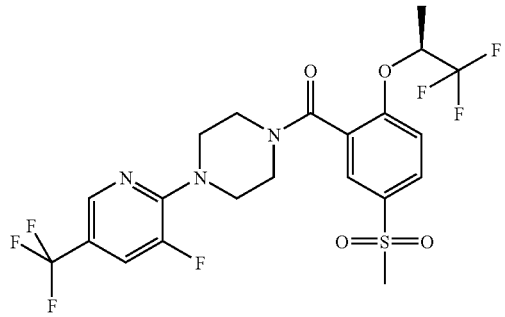

[4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone

[4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone can be isolated, depending upon the method of preparation, as form A, B, C or methylparaben cocrystal form and in an amorphous form.

Forms A, B and C can be isolated from several different crystallization methods of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone as described hereinafter.

The amorphous form can be obtained by lyophilization or fast concentration of a [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone solution as described hereinafter.

The methylparaben cocrystal form can be obtained by, digestion or re-crystallization of form A, B, C or amorphous form and methylparaben as described hereinafter.

In a certain embodiment of the invention, form A can be prepared by method comprising:
  either recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone after seeding;
  or recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and spontaneous crystallization below about 40° C., without seeding.

In a certain embodiment, form A can be obtained by recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in ethanol at certain temperature and concentration after seeding with subsequent crystallization during cooling. Form A can be obtained normally by recrystallization of [4-(3-Fluoro-5-trifluoromethyl-pyridin-2-yl)-piperazin-1-yl]-[5-methanesulfonyl-2-((S)-2, 2,2-trifluoro-1-methyl-ethoxy)-phenyl]-methanone in ethanol and spontaneous crystallization below 40° C., without seeding, with subsequent precipitation during cooling. However the formation of form A is not limited to ethanol, ethanol/water, methanol, methanol/water, toluene, 2-propanole, dioxane/water and dioxane.

These methods of preparation and in particular the preparation of seeding crystals are further described in the examples hereinafter.

Form A is a solvent-free form as no significant weight loss is observed in the TGA curve prior to decomposition.

Form A can be characterized by at least three peaks selected from the following X-ray diffraction peaks obtained with a CuKα radiation expressed in degrees 2Theta at approximately: 13.1, 14.3, 15.4, 16.2, 17.1, 17.2, 17.6, 18.0, 19.8, 20.1, 20.4, 21.0, 22.6, 24.3.

Form A can be characterized by at least five peaks selected from the following X-ray diffraction peaks obtained with a CuKα radiation expressed in degrees 2Theta at approximately: 13.1, 14.3, 15.4, 16.2, 17.1, 17.2, 17.6, 18.0, 19.8, 20.1, 20.4, 21.0, 22.6, 24.3.

Form A can be characterized by at least seven peaks selected from the following X-ray diffraction peaks obtained with a CuKα radiation expressed in degrees 2Theta at approximately: 13.1, 14.3, 15.4, 16.2, 17.1, 17.2, 17.6, 18.0, 19.8, 20.1, 20.4, 21.0, 22.6, 24.3.

Form A can also be characterized by the following X-ray diffraction peaks obtained with a CuKα radiation expressed in degrees 2Theta at approximately: 13.1, 14.3, 15.4, 16.2, 17.1, 17.2, 17.6, 18.0, 19.8, 20.1, 20.4, 21.0, 22.6 and 24.3.

The term "approximately" means in this context that there is an uncertainty in the measurements of the degrees 2Theta of ±0.2 (expressed in degrees 2Theta). Form A can also be characterized by the X-ray diffraction pattern as substantially shown in FIG. 1.

Form A can also be characterized by an infrared spectrum having sharp bands at 3032, 1645, 1623, 1600, 1581, 1501, 1342, 1331, 1314, 1291, 1266, 1245, 1154, 1130, 1088, 1054, 1012, 976, 951, 922, 889, 824, 787, 758, 739, 714 and 636 cm$^{-1}$ (±3 cm$^{-1}$).

Figure 2:
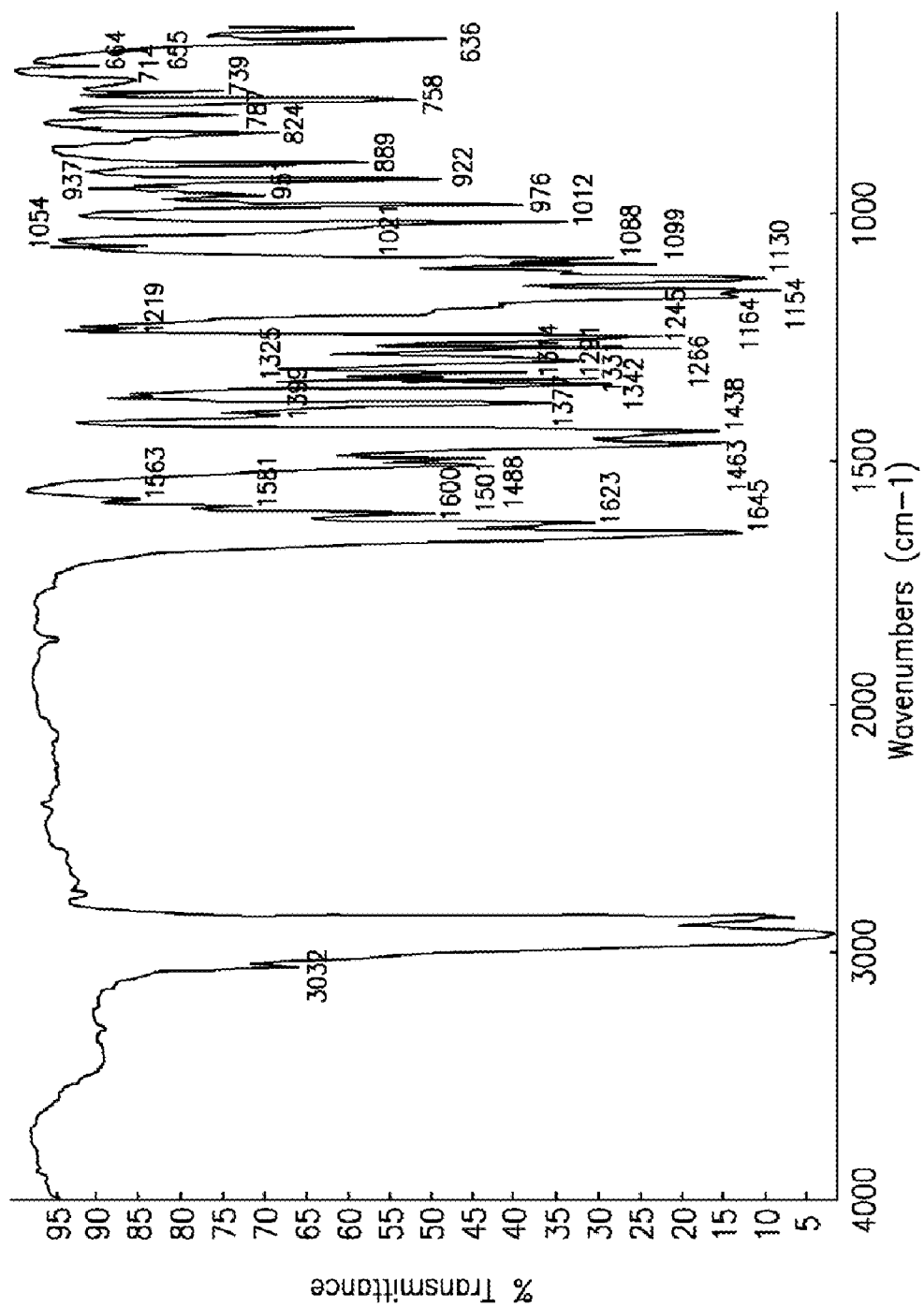
FIG. 2: shows an IR (Infra Red Spectroscopy) spectrum of a typical lot of form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 3:
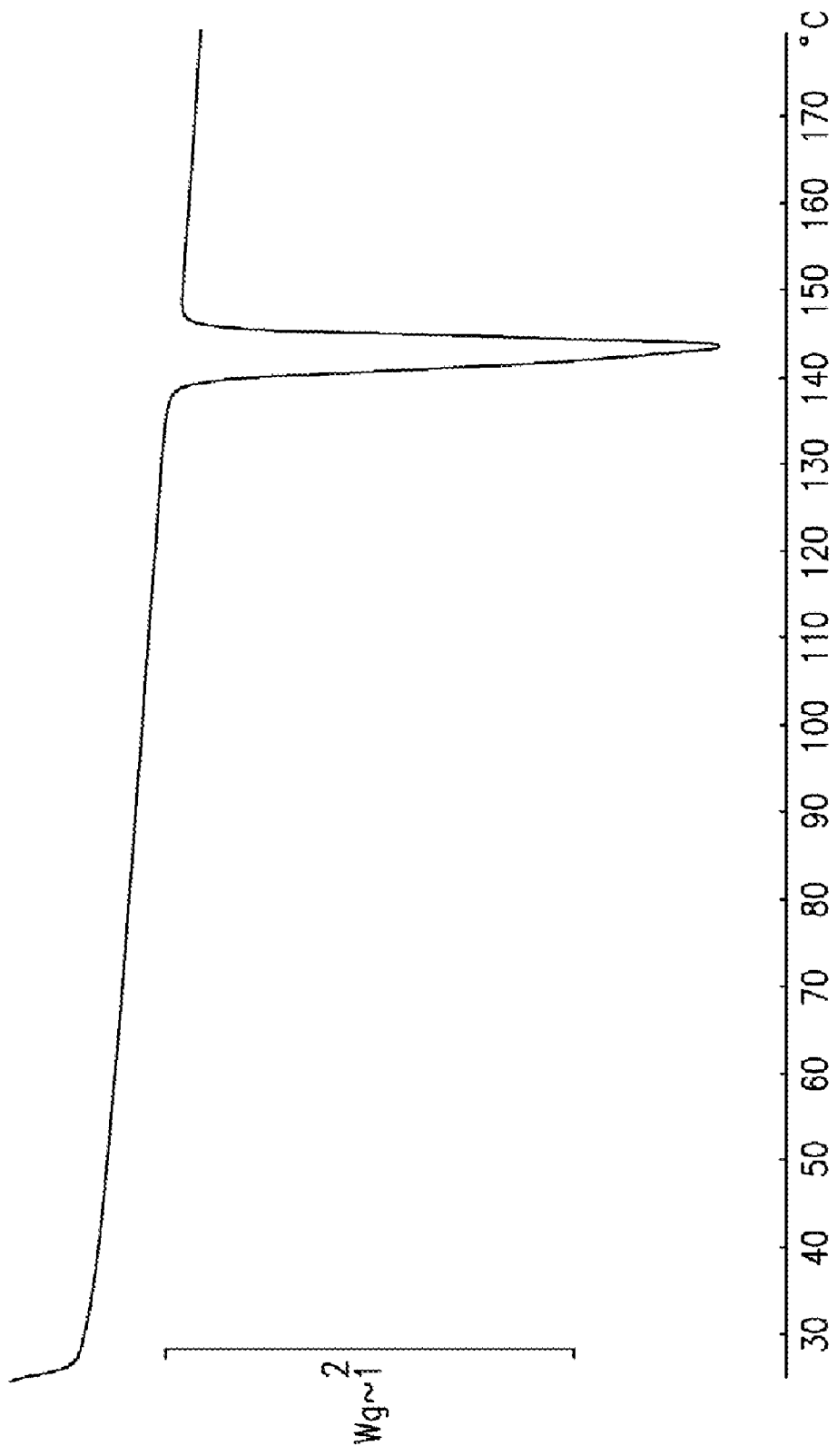
FIG. 3: shows a DSC (Differencial Scanning Calorimetry) curve of a typical lot of form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 4:
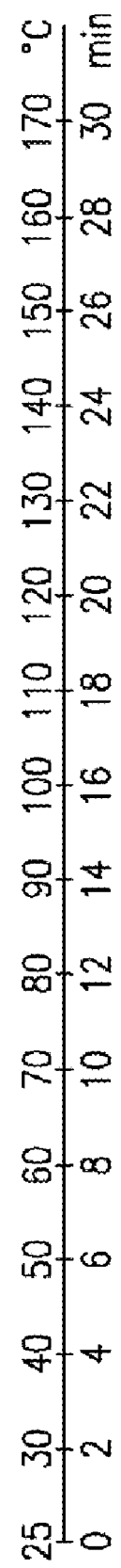
FIG. 4: shows a TGA (Thermo Gravimetric Analysis) curve of a typical lot of form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Form A can also be characterized by the infrared spectrum as substantially shown in FIG. 2.

Form A can also be characterized by a melting point with onset temperature (DSC) in the range of about 138° C. to 144° C.

These characteristics and others are shown in FIGS. 1 to 4.

A single crystal structure analysis of form A was conducted. Table 1 lists the crystal structure data. The experimental XRPD pattern collected with the form A corresponds to the theoretical pattern calculated from crystal structure data. In the single crystal structure of form A the piperazine ring shows chair conformation with the pyridine substituent standing in equatorial position.

TABLE 1

Crystal structure data for form A crystal

| Name | Form A |
|---|---|
| Empirical Formula | $C_{21}H_{20}F_7N_3O_4S$ |
| Formula weight | 543.46 |
| Temperature | 88 K |
| Space group | P2(1)2(1)2 |
| Unit cell dimensions | a = 45.050(9) A |
| | alpha = 90 deg. |
| | B = 8.3500(17) A |
| | beta = 90 deg. |
| | C = 12.380(3) A |
| | gamma = 90 deg. |
| Cell volume | 4657.0(16) A$^3$ |
| Molecules in unit cell | 8 |
| Calculated density | 1.550 g/cm$^3$ |

In one embodiment of the invention, the compound [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprises at least 70% of a crystalline polymorph of form A as described above; in a certain embodiment, it comprises at least 90% of a crystalline polymorph of form A as described above; in a certain embodiment, it comprises at least 96% of a crystalline polymorph of form A as described above; in a certain embodiment, it comprises at least 99% of a crystalline polymorph of form A as described above.

In a certain embodiment of the invention, form B can be prepared by a method comprising:
either seeding of a solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone;

or crystallization of a solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone without seeding;

or recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in one or more solvents and seeding with form B.

Form B can be obtained by seeding of an ethanol solution and subsequent cooling. Form B can be obtained occasionally without seeding of an ethanol solution and subsequent cooling. Form B can also be prepared by re-crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in several solvents and seeding with form B.

Form B is a solvent-free form as no significant weight loss is observed in the TGA curve prior to decomposition.

These methods of preparation and in particular the preparation of seeding crystals are further described in the examples hereinafter.

Form B can be characterized by at least three peaks selected from the following X-ray diffraction peaks obtained with a CuKα radiation expressed in degrees 2Theta at approximately: 11.4, 15.4, 16.2, 16.2, 16.4, 17.8, 18.3, 19.2, 20.1, 21.0, 22.0, 22.5, 26.4.

Form B can be characterized by at least five peaks selected from the following X-ray diffraction peaks obtained with a CuKα radiation expressed in degrees 2Theta at approximately: 11.4, 15.4, 16.2, 16.2, 16.4, 17.8, 18.3, 19.2, 20.1, 21.0, 22.0, 22.5, 26.4.

Form B can be characterized by at least seven peaks selected from the following X-ray diffraction peaks obtained with a CuKα radiation expressed in degrees 2Theta at approximately: 11.4, 15.4, 16.2, 16.2, 16.4, 17.8, 18.3, 19.2, 20.1, 21.0, 22.0, 22.5, 26.4.

Form B can also be characterized by the following X-ray diffraction peaks obtained with a CuKα radiation expressed in degrees 2Theta at approximately: 11.4, 15.4, 16.2, 16.2, 16.4, 17.8, 18.3, 19.2, 20.1, 21.0, 22.0, 22.5 and 26.4.

The term "approximately" means in this context that there is an uncertainty in the measurements of the degrees 2Theta of ±0.2 (expressed in degrees 2Theta).

Figure 5:
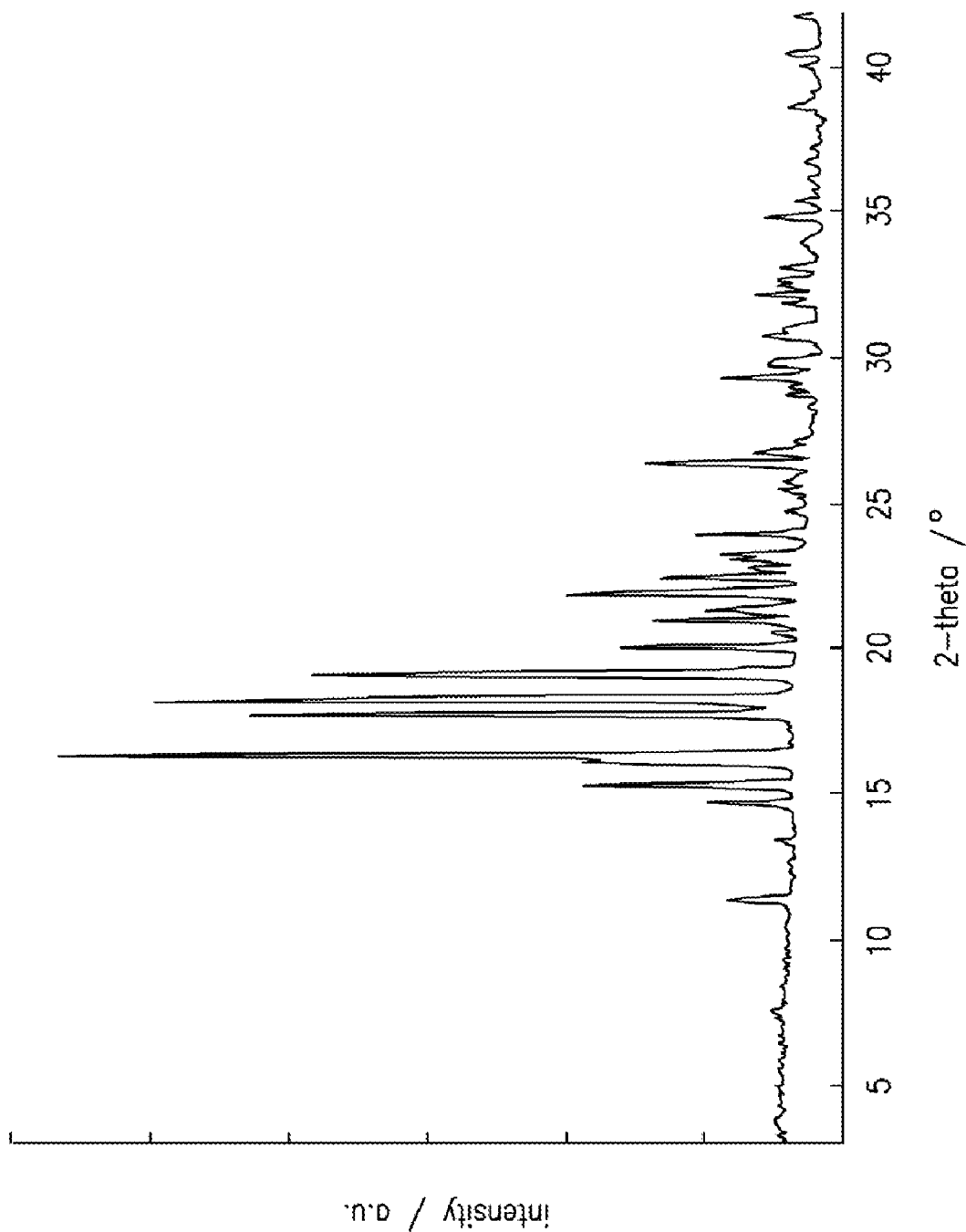
FIG. 5: shows a XRPD (Powder X-Ray Diffraction) pattern of a typical lot of form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Form B can also be characterized by the X-ray diffraction pattern as substantially shown in FIG. 5.

Form B can also be characterized by an infrared spectrum having sharp bands at: 1644, 1635, 1621, 1599, 1567, 1514, 1488, 1398, 1343, 1328, 1291, 1266, 1183, 1155, 1090, 1022, 1003, 973, 958, 938, 920, 897, 822, 783, 753, 740, 683 and 638 cm$^{-1}$ (±3 cm$^{-1}$).

Figure 6:
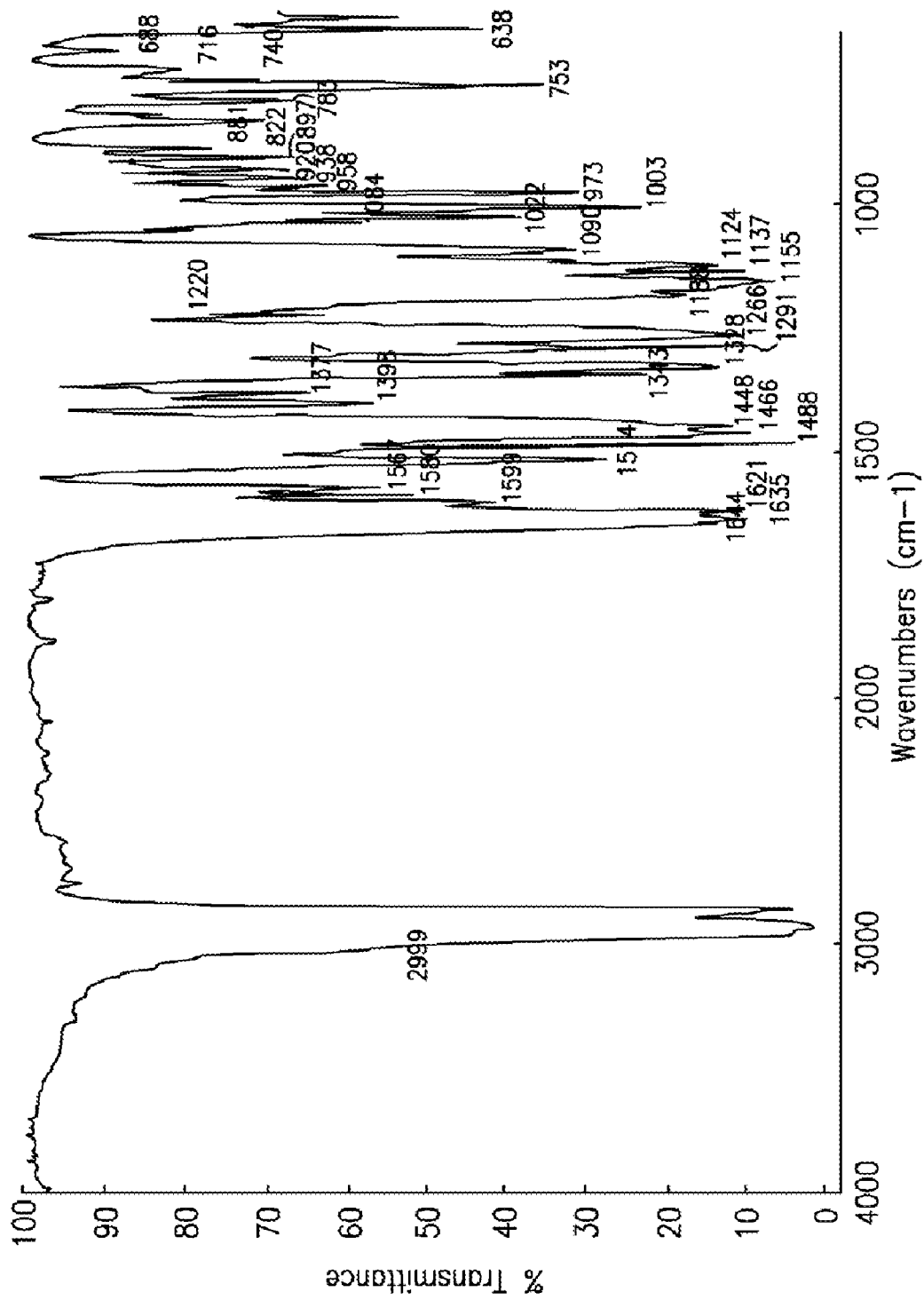
FIG. 6: shows an IR (Infra Red) spectrum of a typical lot of form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 7:
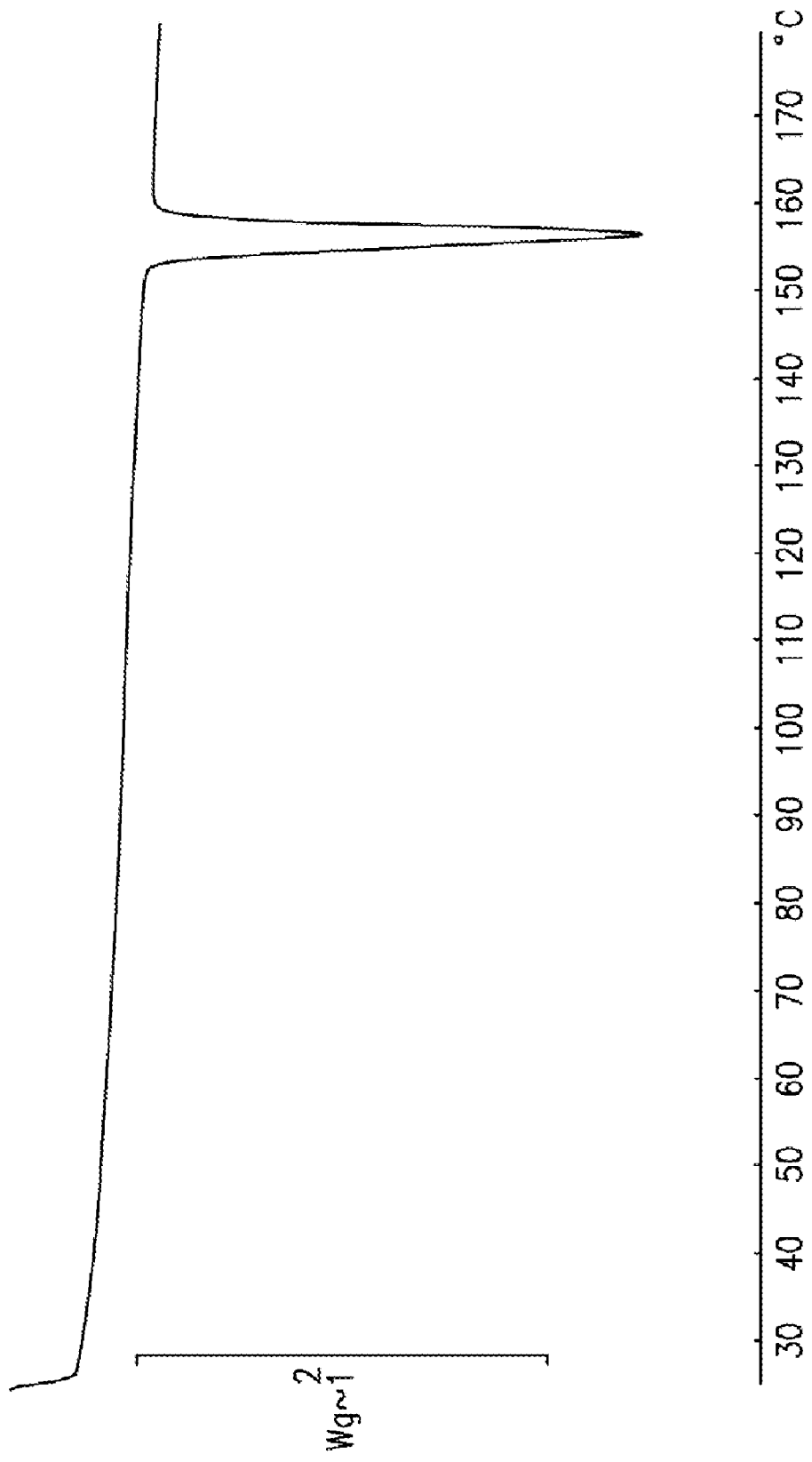
FIG. 7: shows a DSC (Differencial Scanning Calorimetry) curve of a typical lot of form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 8:
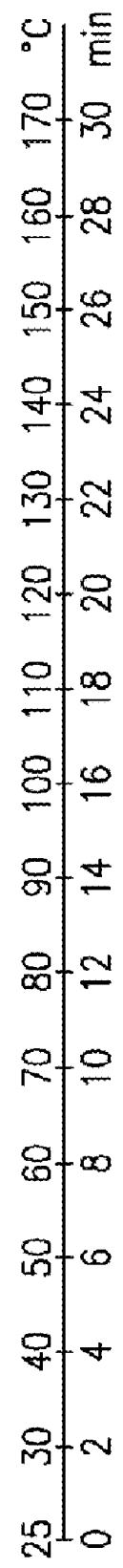
FIG. 8: shows a TGA (Thermo Gravimetric Analysis) curve of a typical lot of form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Form B can also be characterized by an infrared spectrum as substantially shown in FIG. 6.

Form B can also be characterized by a melting point with onset temperature (DSC) in the range of about 151° C. to 154° C.

These characteristics and others are shown in FIGS. 5 to 8.

A single crystal structure analysis of form B was conducted. Table 2 lists the crystal structure data. The experimental XRPD pattern collected with the form B corresponds to the theoretical pattern calculated from crystal structure data. In the single crystal structure of form B the piperazine ring shows chair conformation with the pyridine substituent standing in axial position.

TABLE 2

Crystal structure data for the form B crystal

| Name | Form B |
| --- | --- |
| Empirical Formula | $C_{21}H_{20}F_7N_3O_4S$ |
| Formula weight | 543.46 |
| Temperature | 88 K |
| Space group | P2(1) |
| Unit cell dimensions | A = 16.420(3) Å |
|  | alpha = 90 deg. |
|  | B = 6.1000(12) Å |
|  | beta = 106.49(3) deg. |
|  | C = 23.750(5) Å |
|  | gamma = 90 deg. |
| Cell volume | 2281.0(8) Å$^3$ |
| Molecules in unit cell | 4 |
| Calculated density | 1.583 g/cm$^3$ |

In one embodiment of the invention, the compound [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprises at least 70% of a crystalline polymorph of form B as described above, in a certain embodiment, it comprises at least 90% of a crystalline polymorph of form B as described above; in a certain embodiment, it comprises at least 96% of a crystalline polymorph of form B as described above; in a certain embodiment, it comprises at least 99% of a crystalline polymorph of form B as described above.

In a certain embodiment of the invention, form C can be prepared by a method comprising:
either crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone;
or by crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone by seeding with form C;
or by tempering of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone at about 150° C. and subsequent cooling.

Form C can be obtained by crystallization from a toluene or toluene/n-heptane solution at 100° C. Form C can also be prepared by crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in several solvents and seeding with form C.

Furthermore form C can be obtained by tempering of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone at 150° C. for 2 hours and subsequent rapid cooling.

These methods of preparation and in particular the preparation of seeding crystals are further described in the examples hereinafter.

Form C is a solvent-free form as no significant weight loss is observed in the TGA curve prior to decomposition.

Form C can be characterized by at least three peaks selected from the following X-ray diffraction peaks obtained with a CuKα radiation expressed in degrees 2Theta at approximately: 14.9, 15.7, 16.7, 17.7, 17.8, 18.7, 19.7, 21.8, 22.0, 25.2.

Form C can be characterized by at least five peaks selected from the following X-ray diffraction peaks obtained with a CuKα radiation expressed in degrees 2Theta at approximately: 14.9, 15.7, 16.7, 17.7, 17.8, 18.7, 19.7, 21.8, 22.0, 25.2.

Form C can be characterized by at least seven peaks selected from the following X-ray diffraction peaks obtained with a CuKα radiation expressed in degrees 2Theta at approximately: 14.9, 15.7, 16.7, 17.7, 17.8, 18.7, 19.7, 21.8, 22.0, 25.2.

Form C can also be characterized by the following X-ray diffraction peaks obtained with a CuKα radiation expressed in degrees 2Theta at approximately: 14.9, 15.7, 16.7, 17.7, 17.8, 18.7, 19.7, 21.8, 22.0 and 25.2.

The term "approximately" means in this context that there is an uncertainty in the measurements of the degrees 2 Theta of ±0.2 (expressed in degrees 2 Theta).

Figure 9:
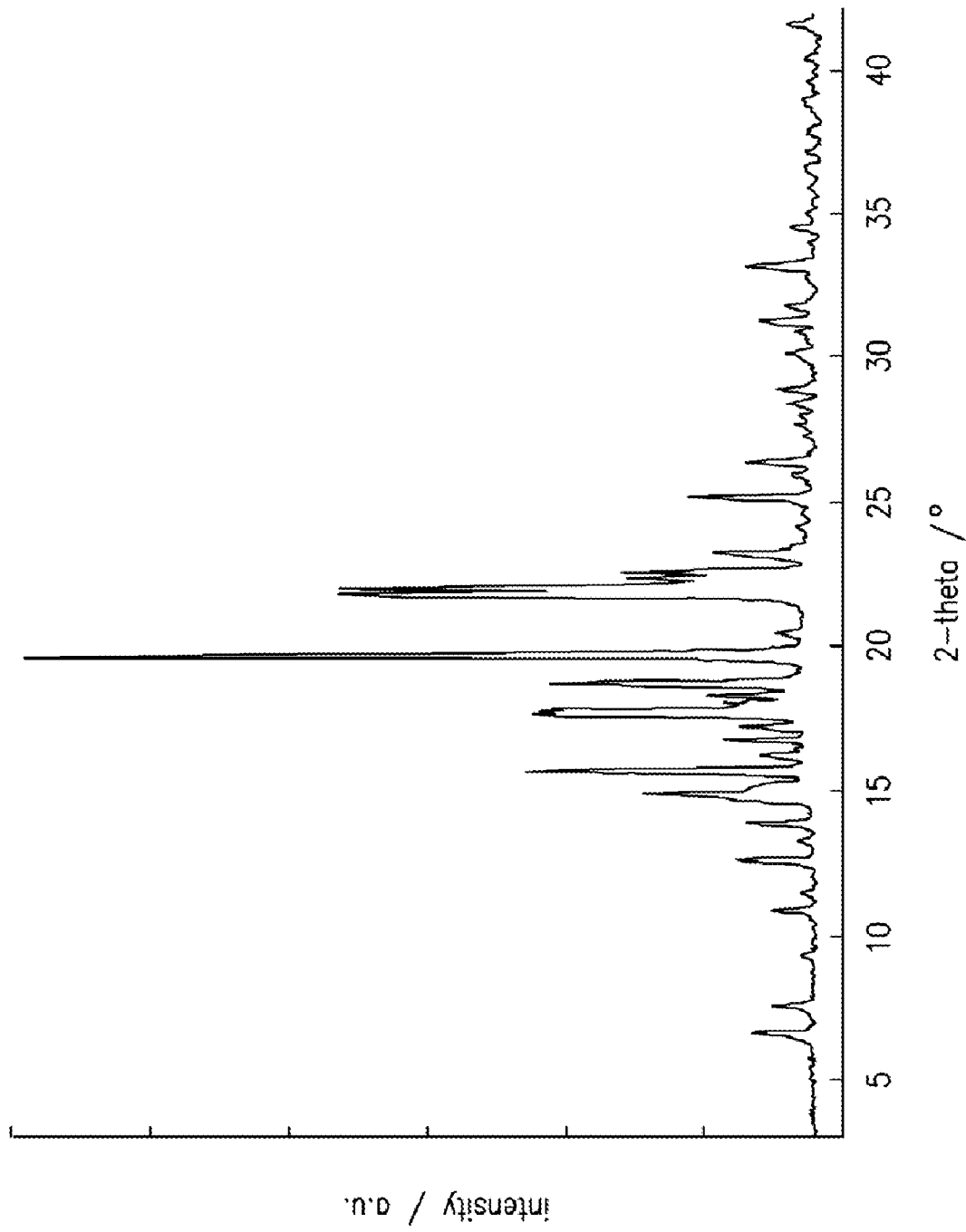
FIG. 9: shows a XRPD (Powder X-Ray Diffraction) pattern of a typical lot of form C of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Form C can also be characterized by the X-ray diffraction pattern as substantially shown in FIG. 9.

Form C can also be characterized by an infrared spectrum having sharp bands at: 1641, 1622, 1601, 1581, 1566, 1514, 1398, 1378, 1341, 1322, 1309, 1294, 1281, 1159, 1087, 1023, 1009, 966, 934, 917, 901, 822, 784, 757, 681 and 640 cm$^{-1}$ (±3 cm$^{-1}$).

Figure 10:
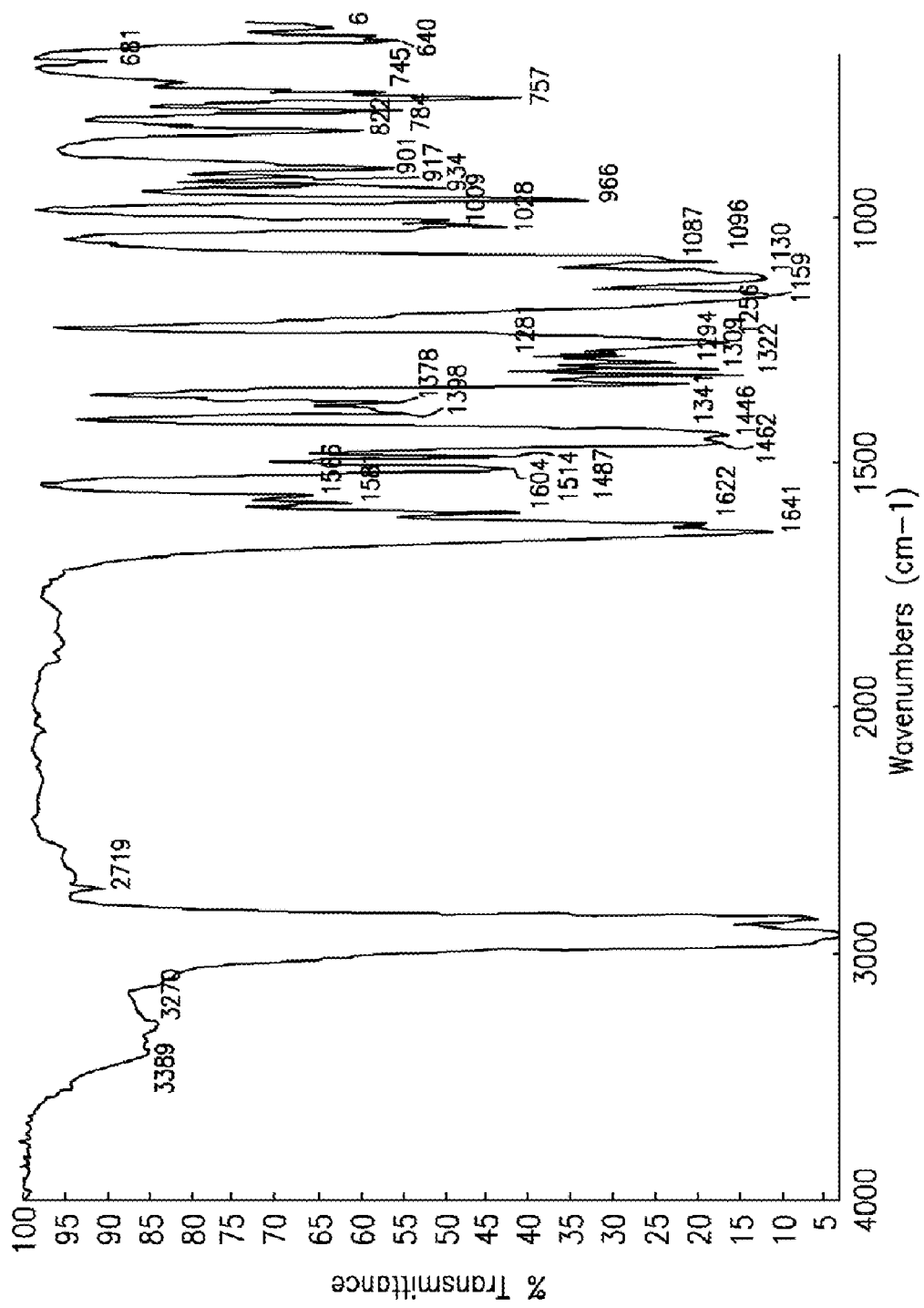
FIG. 10: shows an IR (Infra Red) spectrum of a typical lot of form C of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 11:
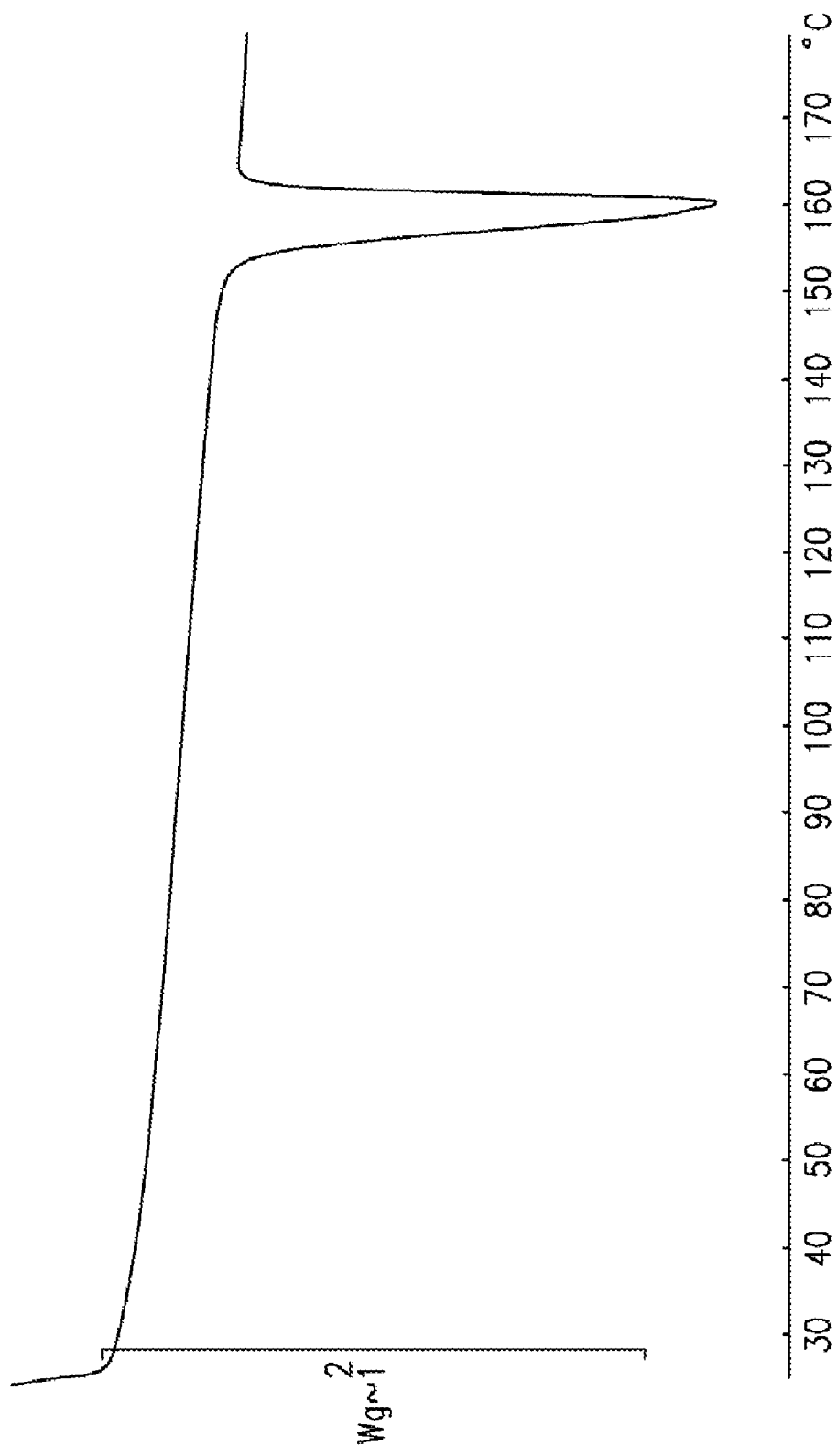
FIG. 11: shows a DSC (Differential Scanning Calorimetry) curve of a typical lot of form C of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 12:
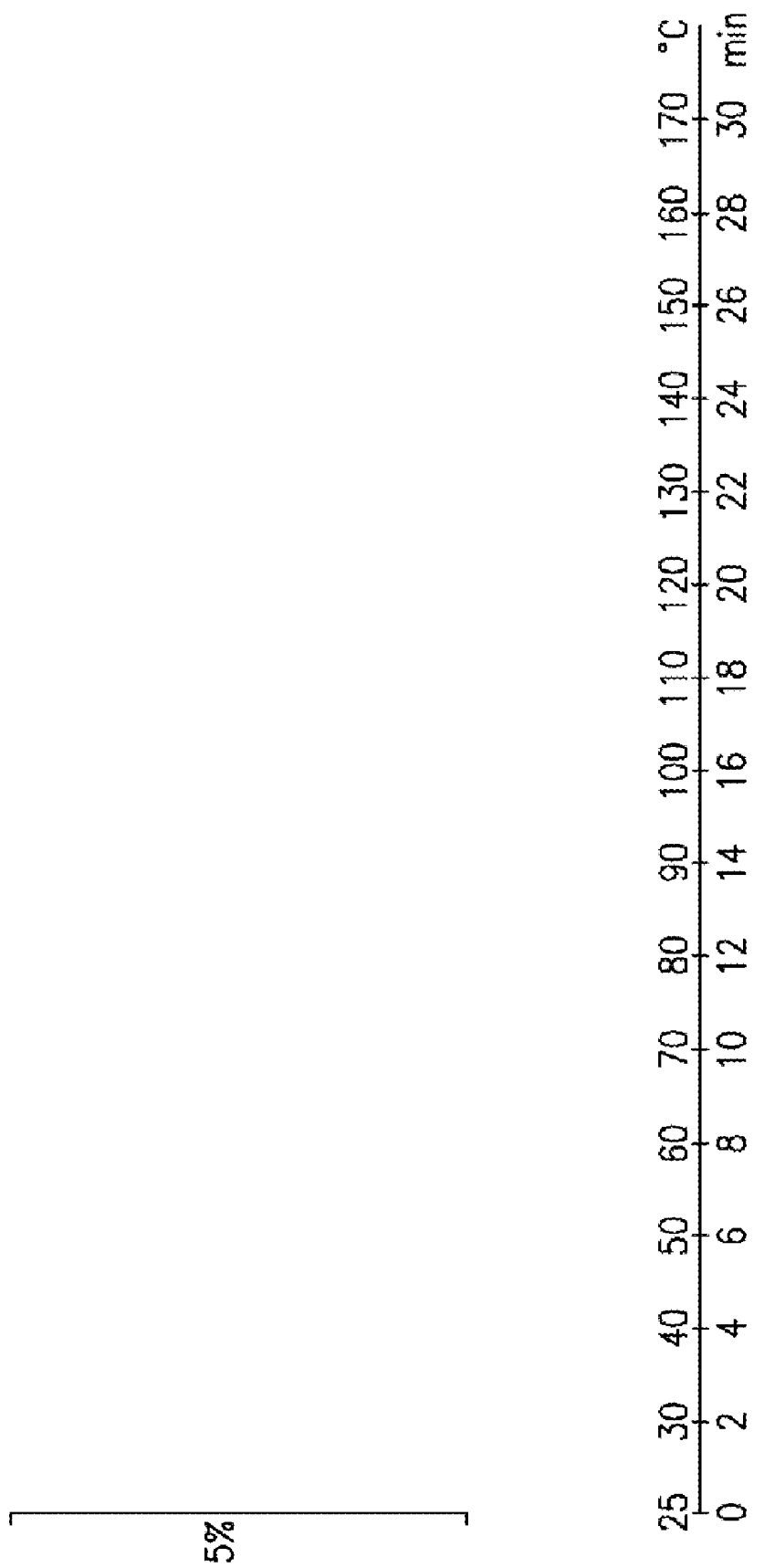
FIG. 12: shows a TGA (Thermo Gravimetric Analysis) curve of a typical lot of form C of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Form C can also be characterized by infrared spectrum as substantially shown in FIG. 10.

Form C can also be characterized by a melting point with onset temperature (DSC) in the range of about 152° C. to 156° C.

These characteristics and others are shown in FIGS. 9 to 12.

In one embodiment of the invention, the compound [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprises at least 70% of a crystalline polymorph of form C as described above; in a certain embodiment, it comprises at least 90% of a crystalline polymorph of form C as described above; in a certain embodiment, it comprises at least 96% of a crystalline polymorph of form C as described above; in a certain embodiment, it comprises at least 99% of a crystalline polymorph of form C as described above.

In a certain embodiment of the invention, the amorphous form can be prepared by a method comprising:
either fast evaporation from a solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone at about 40° C. under vacuum;
or lyophilization of a solution of a solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

The amorphous form can be obtained from an ethanol solution upon fast evaporation at about 40° C. under vacuum. The amorphous form can also be obtained by lyophilization of a solution of 1.0 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in 50 mL acetonitrile (condensator at −46° C. and vacuum at 0-1 mbar)

These methods of preparation of the amorphous form are further described in the examples hereinafter.

The amorphous form can be characterized by the lack of sharp X-ray diffraction peaks in its XRPD pattern.

Figure 13:
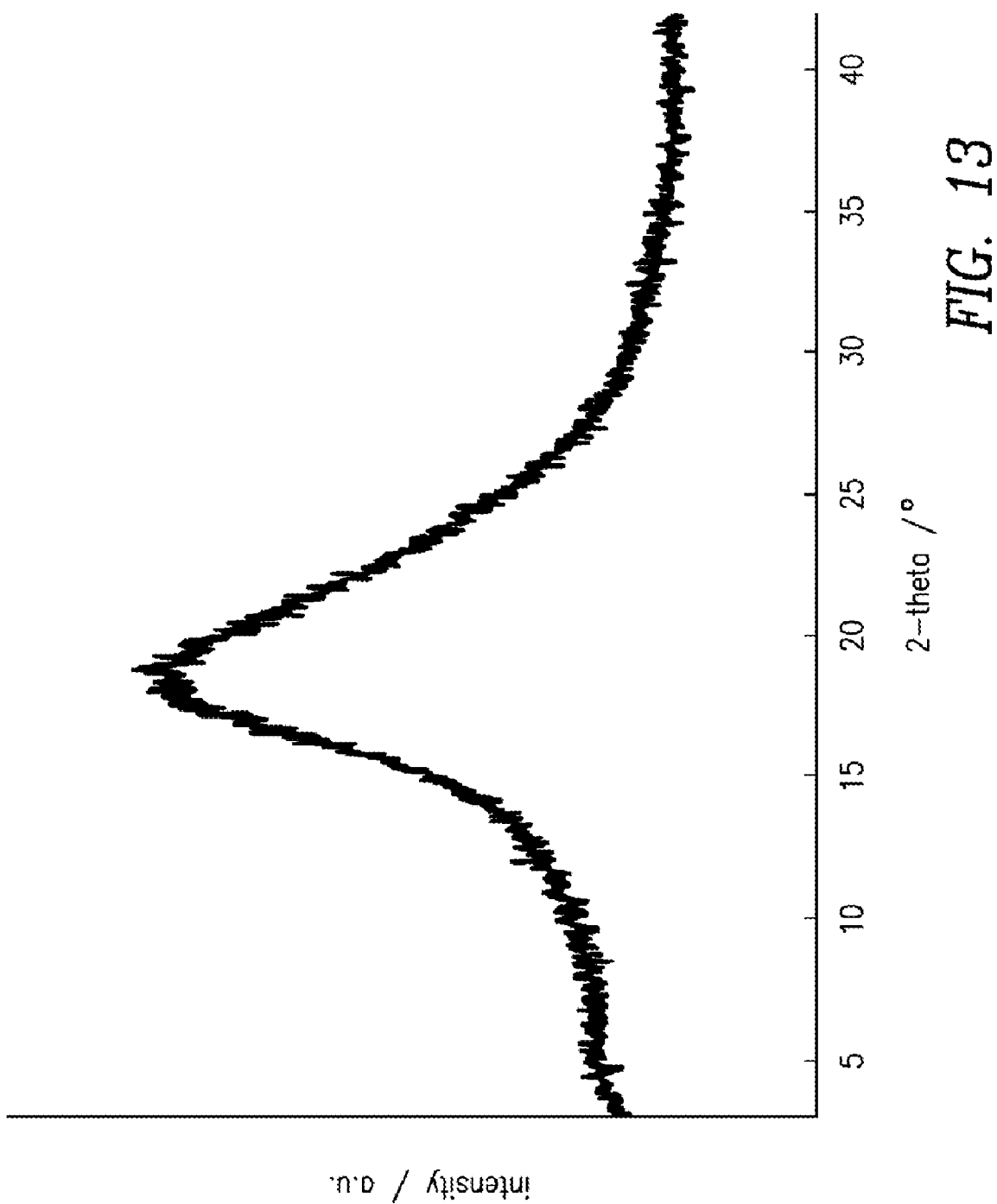
FIG. 13: shows a XRPD (Powder X-Ray Diffraction) pattern of a typical lot of the amorphous form of [4-(3-Fluoro- 5-trifluoromethyl-pyridin-2-yl)-piperazin-1-yl]-[5-methane-sulfonyl-2-((S)-2,2,2-trifluoro-1-methyl-ethoxy)-phenyl]-methanone.

The amorphous form can also be characterized by the X-ray diffraction pattern as substantially shown in FIG. 13.

The amorphous form can be also be characterized by an infrared spectrum having sharp bands at 1642, 1622, 1599, 1579, 1509, 1487, 1399, 1329, 1293, 1253, 1159, 1124, 1090, 1016, 960, 920, 903, 889, 827, 782, 763, 739 and 636 cm$^{-1}$ (±3 cm$^{-1}$).

Figure 14:
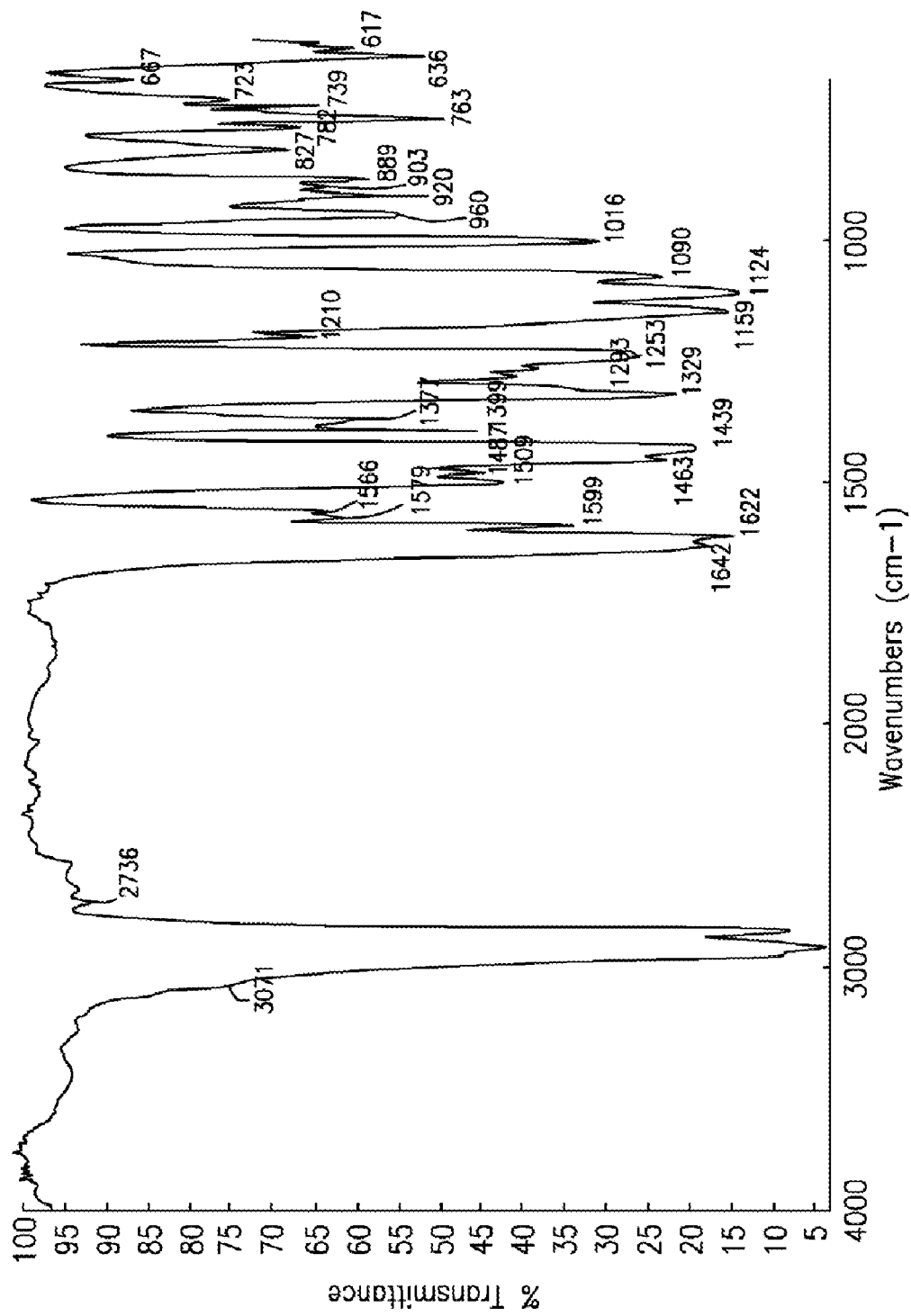
FIG. 14: shows an IR (Infra Red) spectrum of a typical lot of the amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 15:
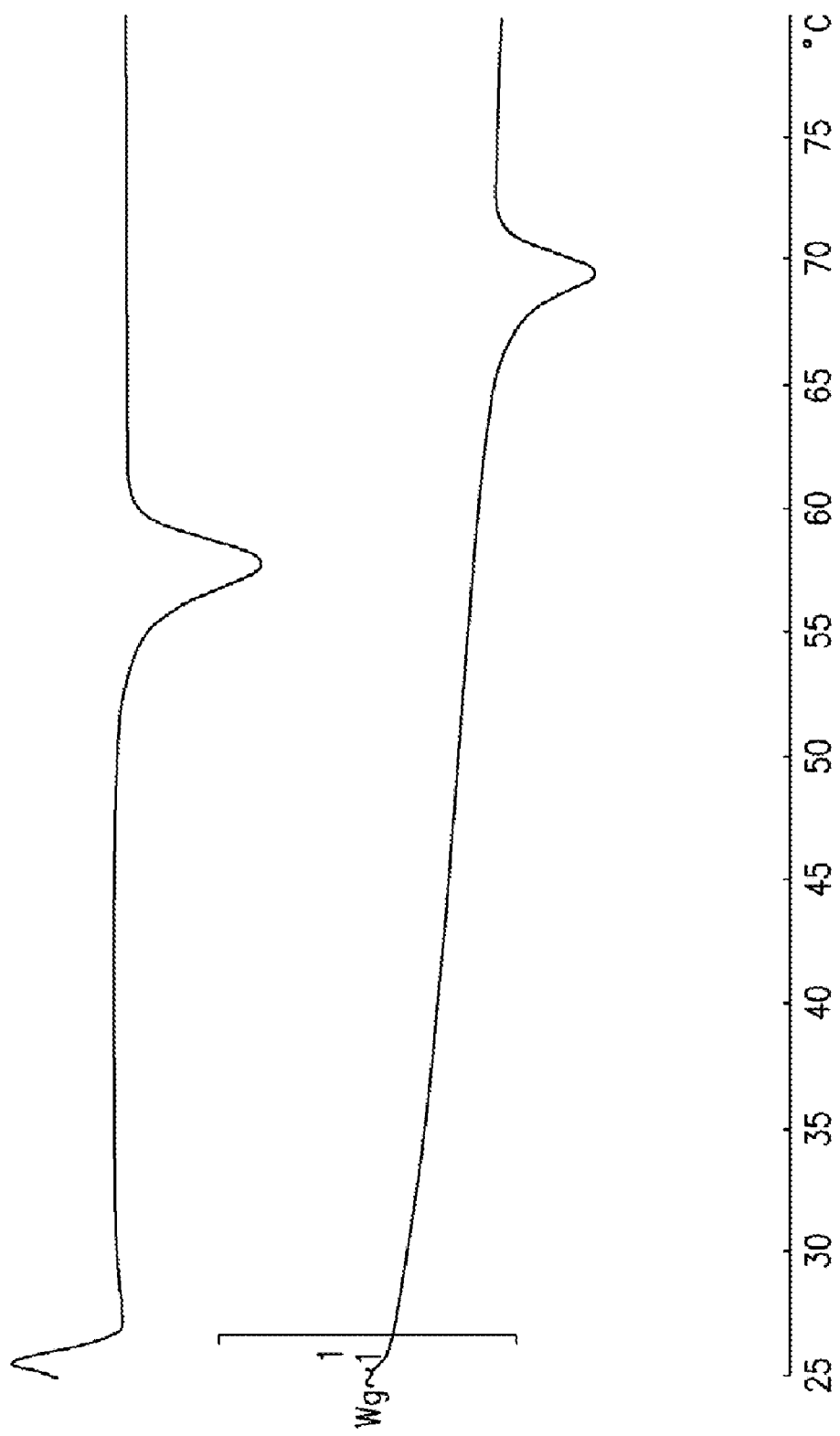
FIG. 15: shows DSC (Differential Scanning Calorimetry) curves of two typical lots of the amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 16:
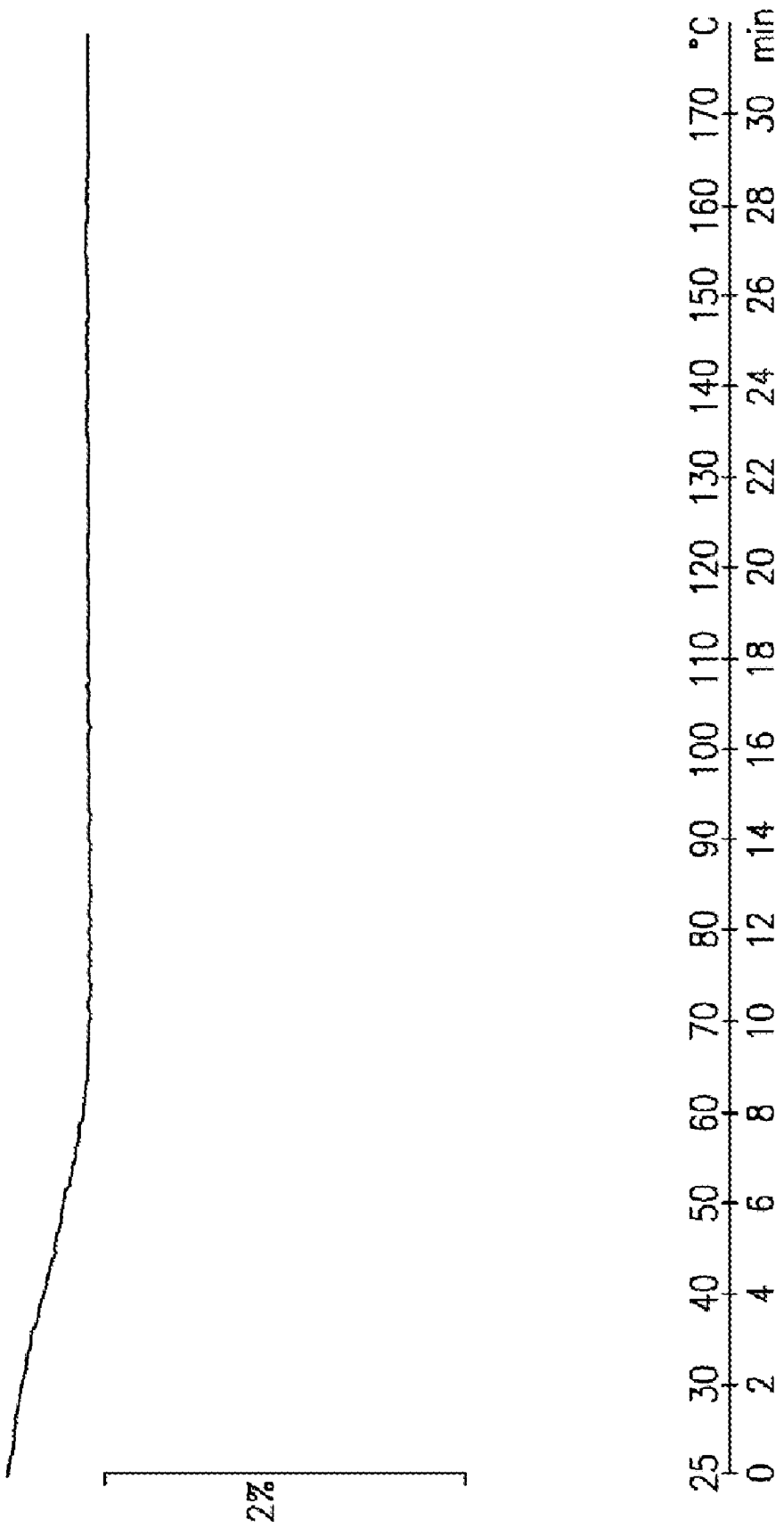
FIG. 16: shows a TGA (Thermo Gravimetric Analysis) curve of a typical lot of the amorphous form of [4-(3-Fluoro-5-trifluoromethyl-pyridin-2-yl)-piperazin-1-yl]-[5-methane-sulfonyl-2-((S)-2,2,2-trifluoro-1-methyl-ethoxy)-phenyl]-methanone.
Figure 17:
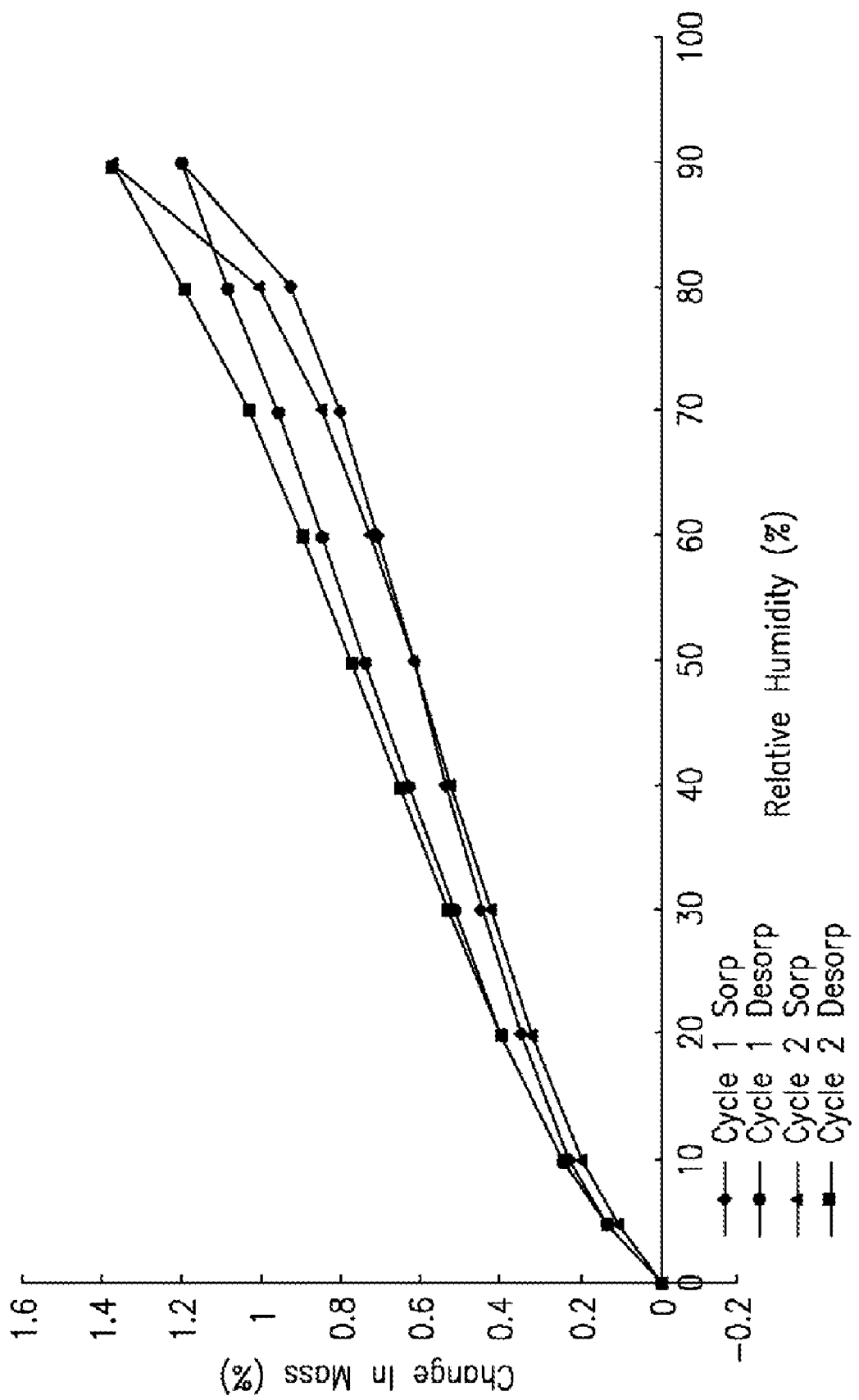
FIG. 17: shows a DVS (Dynamic Vapor Sorption) isotherm of a typical lot of the amorphous form of [4-(3-Fluoro-5-trifluoromethyl-pyridin-2-yl)-piperazin-1-yl]-[5-methane-sulfonyl-2-((S)-2,2,2-trifluoro-1-methyl-ethoxy)-phenyl]-methanone.

The amorphous form can also be characterized by infrared spectrum as substantially shown in FIG. 14.

The amorphous form can be also be characterized by a glass transition temperature (DSC, heating rate 10 K/min, closed pan) of about 48° C. to about 65° C. (The glass transition temperature is largely dependent on the solvent/water content).

These characteristics and others are shown in FIGS. 13 to 17.

In one embodiment of the invention, the compound [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprises at least 70% of an amorphous form as described above; in a certain embodiment, it comprises at least 90% of an amorphous form as described above; in a certain embodiment, it comprises at least 96% of an amorphous form as described above; in a certain embodiment, it comprises at least 99% of an amorphous form as described above.

In a certain embodiment of the invention, the methylparaben cocrystal form can be prepared by a method comprising re-crystallization of form A, B, C or amorphous form and methylparaben with or without seeding in solvent systems.

The methylparaben cocrystal form can be produced by digestion in solvents as e.g. ethanol and water. It can also be prepared by re-crystallization of form A, B, C or amorphous form and methylparaben with or without seeding in solvent systems comprising but not limited to ethanol. 4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone-methylparaben ratio can range from 1:1 to 1:10.

These methods of preparation and in particular the preparation of seeding crystals are further elucidated in the examples hereinafter.

The methylparaben cocrystal form can be characterized by at least three peaks selected from the following X-ray diffraction peaks obtained with a CuKα radiation expressed in degrees 2Theta at approximately: 8.0, 8.9, 10.5, 12.6, 15.2, 16.1, 17.7, 18.5, 19.8, 20.2, 21.7, 22.9, 24.2, 25.9.

The methylparaben cocrystal form can be characterized by at least five peaks selected from the following X-ray diffraction peaks obtained with a CuKα radiation expressed in degrees 2Theta at approximately: 8.0, 8.9, 10.5, 12.6, 15.2, 16.1, 17.7, 18.5, 19.8, 20.2, 21.7, 22.9, 24.2, 25.9.

The methylparaben cocrystal form can be characterized by at least seven peaks selected from the following X-ray diffraction peaks obtained with a CuKα radiation expressed in degrees 2Theta at approximately: 8.0, 8.9, 10.5, 12.6, 15.2, 16.1, 17.7, 18.5, 19.8, 20.2, 21.7, 22.9, 24.2, 25.9.

The methylparaben cocrystal form can also be characterized by the following X-ray diffraction pattern obtained with a CuKα radiation expressed in degrees 2Theta at approximately: 8.0, 8.9, 10.5, 12.6, 15.2, 16.1, 17.7, 18.5, 19.8, 20.2, 21.7, 22.9, 24.2 and 25.9.

The term "approximately" means in this context that there is an uncertainty in the measurements of the degrees 2Theta of ±0.2 (expressed in degrees 2Theta).

Figure 18:
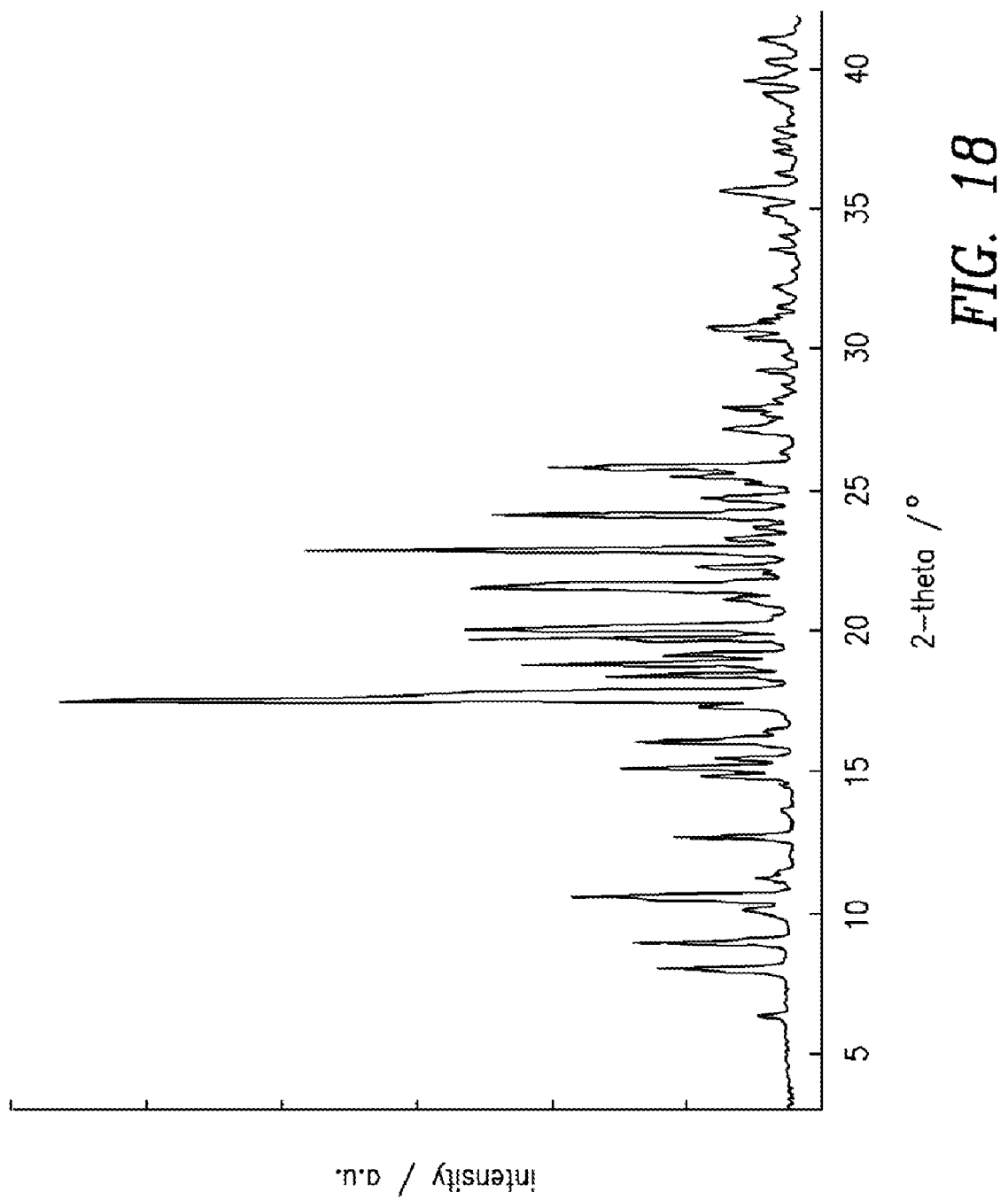
FIG. 18: shows a XRPD (Powder X-Ray Diffraction) pattern of a typical lot of the methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

The methylparaben cocrystal form can also be characterized by the X-ray diffraction pattern as substantially shown in FIG. 18.

The methylparaben cocrystal form can also be characterized by an infrared spectrum having sharp bands at 3154, 3081, 1709, 1614, 1586, 1378, 1337, 1313, 1247, 1189, 1172, 1124, 1085, 1019, 959, 928, 916, 908, 894, 857, 783, 772, 729 and 702 cm$^{-1}$ (±3 cm$^{-1}$).

Figure 19:
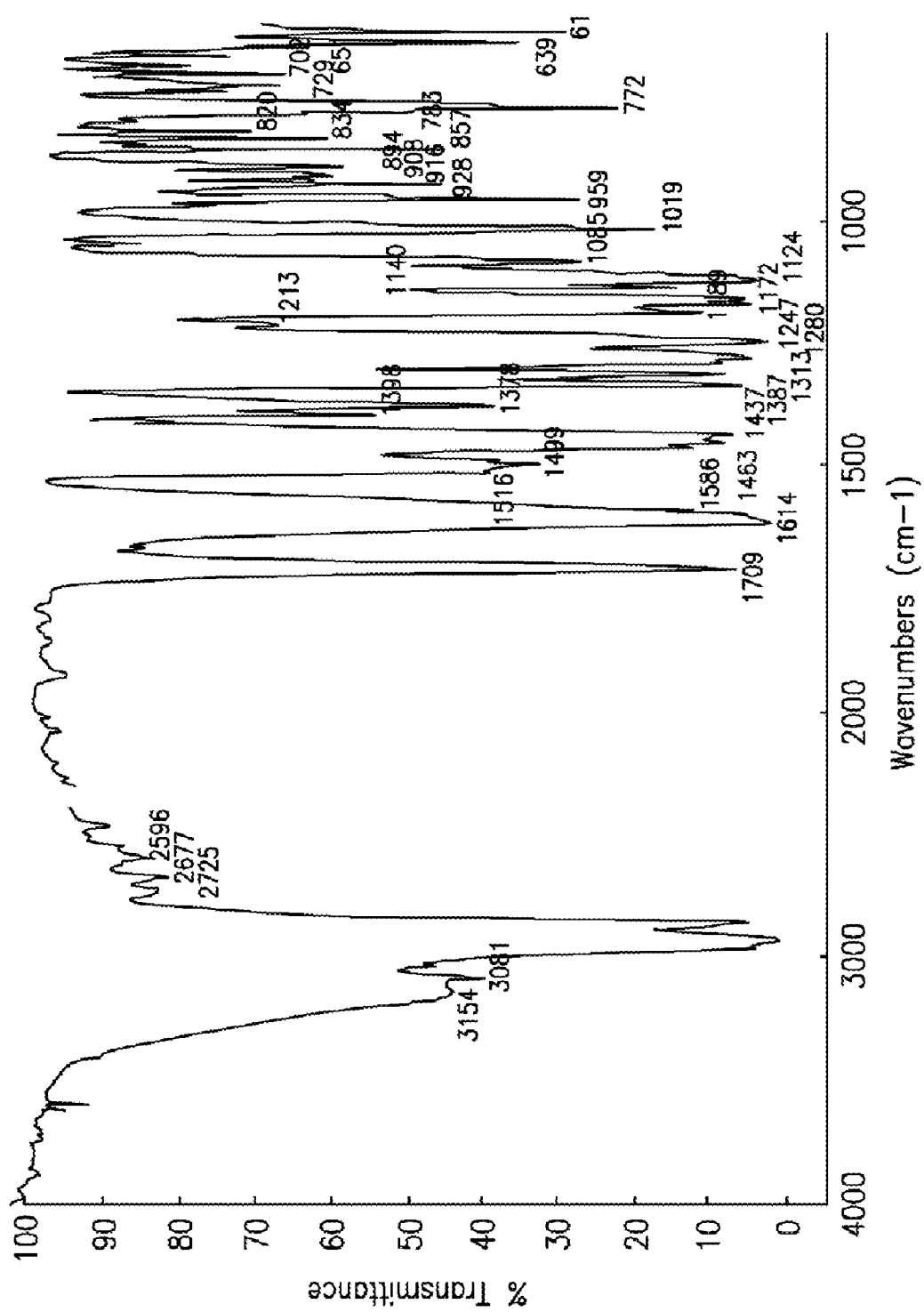
FIG. 19: shows an IR (Infra Red) spectrum of a typical lot of the methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 20:
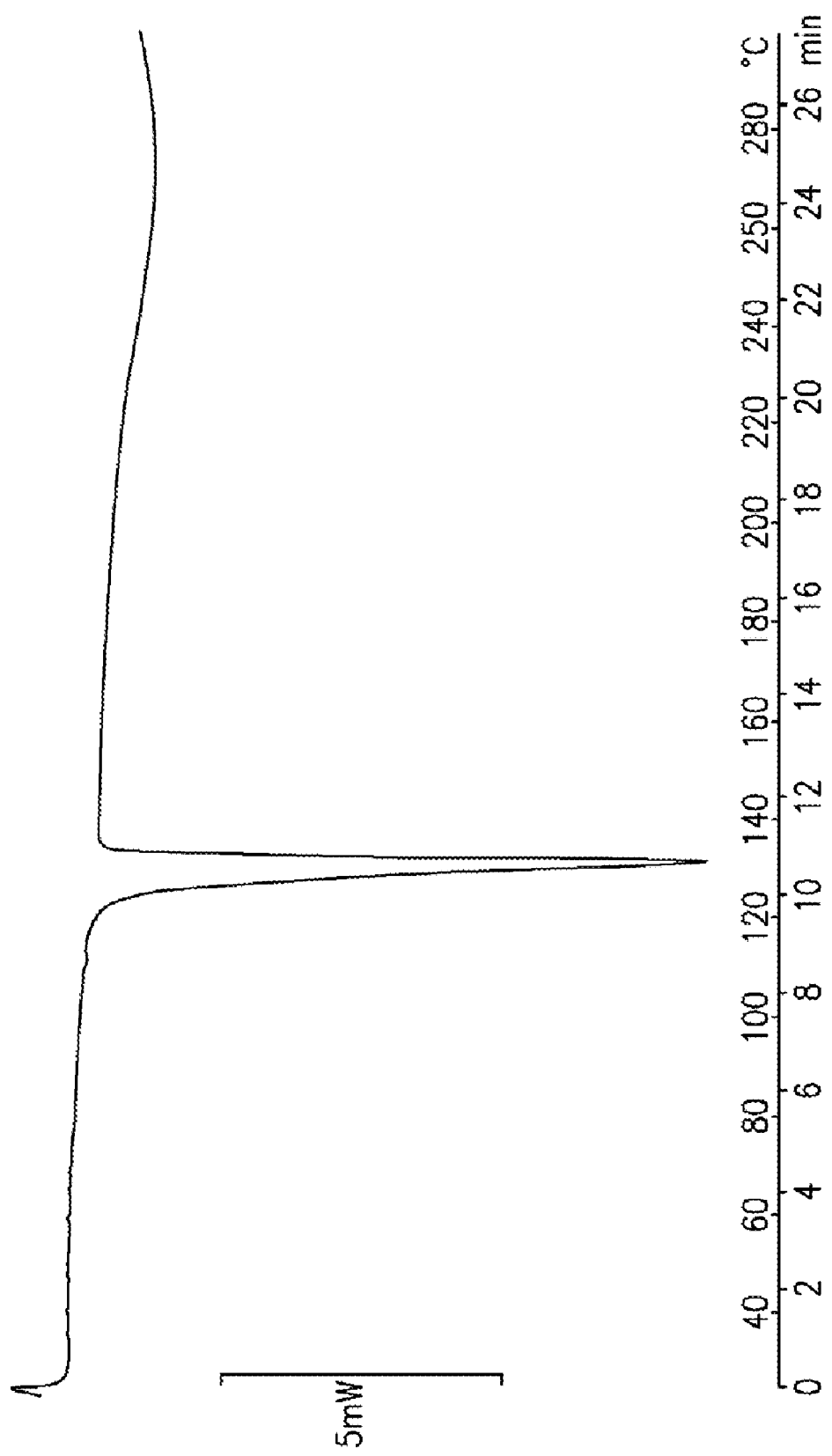
FIG. 20: shows a DSC (Differencial Scanning Calorimetry) curve of a typical lot of the methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.
Figure 21:
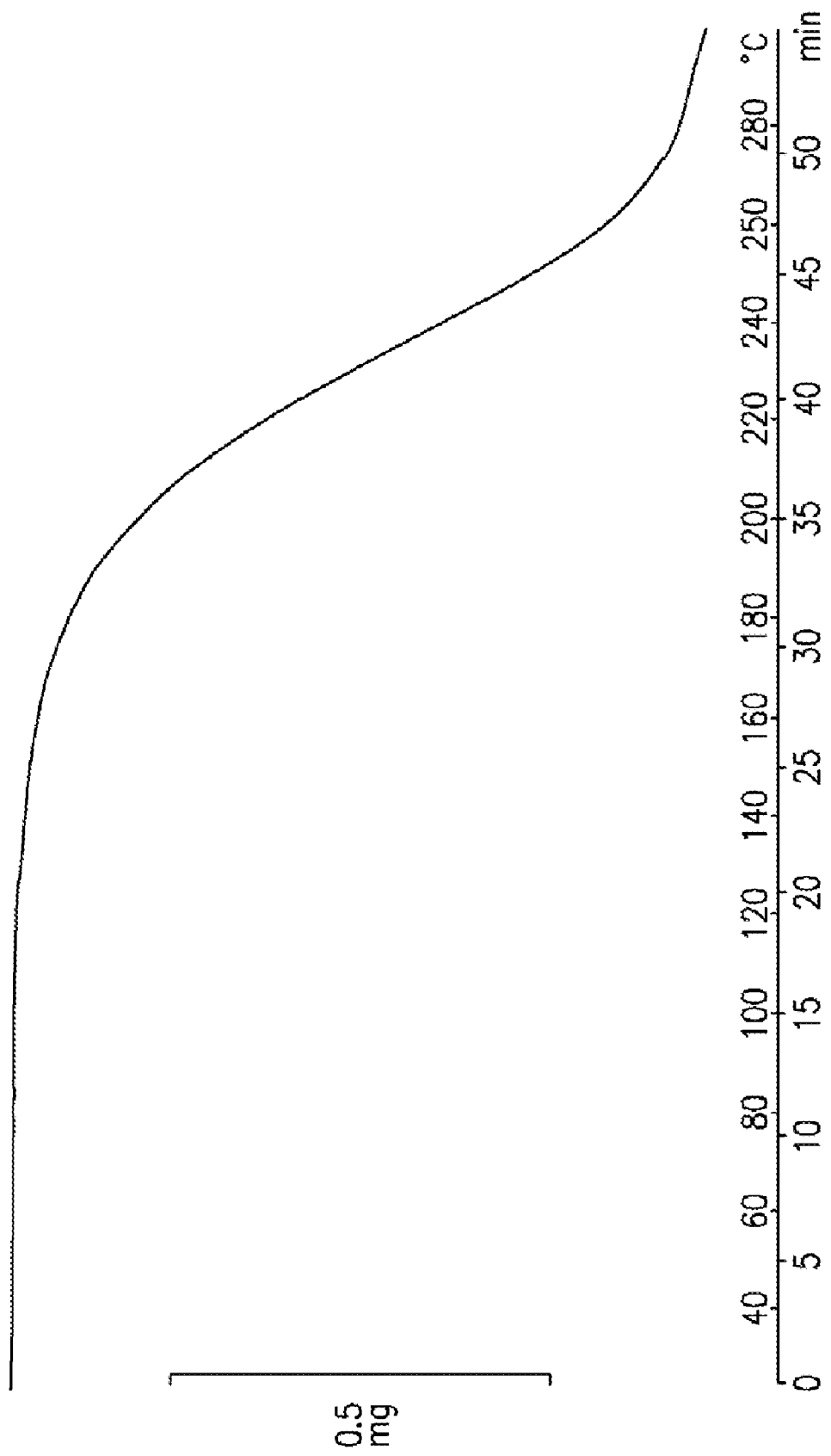
FIG. 21: shows a TGA (Thermo Gravimetric Analysis) curve of a typical lot of the methylparaben cocrystal form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

The methylparaben cocrystal form can also be characterized by the infrared spectrum as substantially shown in FIG. 19.

These characteristics and others are shown in FIGS. 18 to 21.

A single crystal structure analysis of the methylparaben cocrystal was conducted. Table 3 lists the crystal structure data. The experimental XRPD pattern collected with the methylparaben cocrystal corresponds to the theoretical pattern calculated from crystal structure data.

TABLE 3

| Crystal structure data for the methylparaben cocrystal form. | |
|---|---|
| Name | methylparaben cocrystal form |
| Empirical Formula | $C_{29}H_{28}F_7N_3O_7S$ |
| Formula weight | 695.60 |
| Temperature | 89 K |
| Space group | P1 |
| Unit cell dimensions | a = 10.140(2) A |
| | alpha = 83.65(3) deg. |
| | B = 11.690(2) A |
| | beta = 79.88(3) deg. |
| | C = 13.870(3) A |
| | gamma = 72.75(3) deg. |
| Cell volume | 1542.8(5) A$^3$ |
| Molecules in unit cell | 2 |
| Calculated density | 1.497 g/cm$^3$ |

In one embodiment of the invention, the compound comprises at least 70% of a methylparaben cocrystal of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone as described above; in a certain embodiment, it comprises at least 90% of a methylparaben cocrystal as described above; in a certain embodiment, it comprises at least 96% of a methylparaben cocrystal as described above; in a certain embodiment, it comprises at least 99% of a methylparaben cocrystal as described above.

As mentioned hereinabove, in an aspect the invention relates to a pharmaceutical composition comprising one or more of crystalline forms A, B, C or methylparaben cocrystal form or amorphous form as the active ingredient.

Pharmaceutical compositions according to the invention, in addition to one of the crystalline or amorphous forms according to the invention mentioned hereinabove, can contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard shell capsules. Suitable carriers for soft shell capsules are, for example, vegetable oils, waxes, fats, semi-solid and liquid polyols and the like. Depending on the nature of the active substance no carriers are, however, usually required in the case of soft gelatine capsules. Suitable carriers for the solutions include, for example, water, polyols, sucrose, invert sugar, glucose, and the like.

The active ingredient can be formulated at low or high concentrations in a composition further comprising usual pharmaceutically acceptable adjuvants known in the art.

These pharmaceutical compositions can be in the form of tablets, coated tablets, dragées, hard and soft shell capsules, solutions, emulsions or suspensions. The invention also provides a process for the production of such compositions, which comprises bringing the aforementioned modifications and forms into a galenical administration form together with one or more therapeutically inert carriers.

In addition, the pharmaceutical compositions can contain pharmaceutically acceptable preservatives, solubilizers, stabilizers, wetting agents, emulsifiers, sweeteners, colorants, flavoring agents, salts for varying the osmotic pressure, buffers, masking agents or antioxidants. They can also contain still other therapeutically valuable substances.

The dosage at which the active ingredient, i.e. the crystalline or amorphous forms according to the invention that can be administered can vary within wide limits and will, of course, have to be adjusted to the individual requirements in each particular case. In the case of oral administration the dosage for adults can vary from about 0.01 mg to about 1000 mg, preferably from about 1 mg to about 240 mg, and still more preferably from about 3 mg to about 120 mg per day. The daily dosage may be administered as single dose or in divided doses and, in addition, the upper limit can also be exceeded when this is found to be indicated.

The table hereinafter gives an example of a typical capsule formulation which can be prepared according to the invention.

Formulation

Capsule Formulation (Wet Granulation)

TABLE 4

| | Capsule formulation composition | | | | |
|---|---|---|---|---|---|
| | | mg/capsule | | | |
| Item | Ingredients | 1.0 mg | 3.0 mg | 10.0 mg | 25.0 mg | 40.0 mg |
| 1. | Form A of active ingredient | 1.00 | 3.00 | 10.00 | 25.00 | 40.00 |
| 2. | Lactose Monohydrate | 114.00 | 112.00 | 105.00 | 90.00 | 75.00 |
| 3. | Maize Starch | 60.00 | 60.00 | 60.00 | 60.00 | 60.00 |
| 4. | Sodium Starch Glycolate | 10.00 | 10.00 | 10.00 | 10.00 | 10.00 |
| 5. | Povidone 30 | 10.00 | 10.00 | 10.00 | 10.00 | 10.00 |
| 6. | Talc | 4.00 | 4.00 | 4.00 | 4.00 | 4.00 |
| 7. | Magnesium Stearate | 1.00 | 1.00 | 1.00 | 1.00 | 1.00 |
| | Total | 200.00 | 200.00 | 200.00 | 200.00 | 200.00 |

Manufacturing Procedure
1. Mix items 1, 2, 3, 4 and 5 in a suitable mixer.
2. Granulate the mixed powder from step 1 with granulation liquid.
3. Screen the mixture received from step 2, dry and sieve the granules.
4. Add items 6 and 7 to the dried and sieved granules from step 3 and mix.
5. Fill mixture from step 4 into a suitable capsule.

EXAMPLES

Preparation of the Compounds According to the Invention

Example 1

Preparation of Form A

General

Form A can be produced by digestion in solvents as e.g. methanol, ethanol, 2-propanol, isopropylacetate, t-butyl methyl ether, toluene or solvent mixtures as acetone/water (e.g. 1:1, w/w), water/methanol (e.g. 1:1, w/w), water/ethanol (e.g. 0.4:0.6, w/w). It can also be prepared by re-crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone with or without seeding in solvent systems comprising but not limited to ethanol, water/ethanol (e.g. 0.6:0.4, w/w).

Crystallization Procedure 30.0 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were dissolved in 150 g ethanol and heated up to 70° C. The solution was hot filtered. The temperature was reduced to 40-42° C. At 40-42° C. 300 mg of form A seeding crystals of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were added. The temperature was hold for 1 h at 40-42° C. Subsequently the suspension was cooled with 0.3 K/min down to 0 to −5° C. After stirring at 0 to −5° C. for 1 h the crystals were filtered, washed with ca. 20 mL of ethanol (0 to −5° C.) and dried at 50° C./0-20 mbar for 14 h. Yield: 26.31 g (87.7%).

Preparation of Seeding Crystals of Form A

Form A seeding crystals can be prepared by digestion of a slurry of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in solvent systems comprising but not limited to ethanol, methanol and water mixtures of ethanol/water (e.g. 0.4:0.6 w/w). After stirring the slurry at room temperature for several days form A crystals could be filtered and were dried at 50° C./0-20 mbar for 14 h. It might be necessary to repeat this procedure several times.

Solid State Properties of Form A

XRPD-pattern, IR-spectrum, DSC curve, and TG curve of form A are listed in FIGS. 1 to 4.

Example 2

Preparation of Form B

General

Form B can be prepared by re-crystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone with or without seeding in different solvent systems comprising methanol, ethanol, 1,4-dioxane and water mixtures of these.

Crystallization Procedure 30.0 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were dissolved in 150 g ethanol and heated up to 60° C. Dissolution of [4-(3-Fluoro-5-trifluoromethyl-pyridin-2-yl)-piperazin-1-yl]-[5-methanesulfonyl-2-((5)-2,2,2-trifluoro-1-methyl-ethoxy)-phenyl]-methanone occurred between 55-57° C. The solution was hot filtered. The temperature was reduced to 40-42° C. At 40-42° C. 3.0 g (10%-w) of form B seeding crystals of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were added to the clear solution. Subsequently the suspension was cooled down to 5° C. within 5 hours. The crystals were filtered, washed with ca. 10 mL of ethanol (0° C.) and dried at 50° C./0-20 mbar for 14 h. Yield: 29.17 g (88.4%).

Preparation of Seeding Crystals of Form B

Form B seeding crystals can be prepared by rapid cooling of a highly saturated solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in solvent systems comprising but not limited to ethanol, tetrahydrofurane, toluene or 1,4-dioxane. 3.0 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were dissolved in 9 g ethanol and heated up to 70° C. The solution was hot filtered. The temperature of the clear solution was rapidly reduced to 0 to −5° C. The crystals were filtered, washed with ca. 20 mL of ethanol (0 to −5° C.) and dried at 50° C./0-20 mbar for 14 h. It might be necessary to repeat this procedure several times.

Solid State Properties of Form B

XRPD-pattern, IR-spectrum, DSC curve, and TG curve of form B are listed in FIGS. 5 to 8.

Example 3

Preparation of Form C

General

Form C can be produced by digestion in solvents as n-heptane, toluene, o-xylene or solvent mixtures as n-heptane/toluene (e.g. 1:0.8, w/w). It can also be prepared by re-crystallization of [4-(3-Fluoro-5-trifluoromethyl-pyridin-2-yl)-piperazin-1-yl]-[5-methanesulfonyl-2-((5)-2,2,2-trifluoro-1-methyl-ethoxy)-phenyl]-methanone with seeding in different solvent systems.

Crystallization Procedure 45.0 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were digested in 43.4 g toluene and 54.7 g n-heptane and heated up to 98-100° C. The suspension was stirred at 98-100° C. for 48 h. The suspension was hot filtered. The obtained solid residues were dried at 70° C./0-20 mbar for 24 h. Yield: 23.0 g (51.5%).

Solid State Properties of Form C

XRPD-pattern, IR-spectrum, DSC curve, and TG curve of form C are listed in FIGS. 9 to 12.

Example 4

Preparation of the Amorphous Form

General

An amorphous form was accessible from ethanol solution upon fast evaporation at approx. 40° C. under vacuum. Further amorphous form of [4-(3-Fluoro-5-trifluoromethyl-pyridin-2-yl)-piperazin-1-yl]-[5-methanesulfonyl-2-((5)-2,2,2-trifluoro-1-methyl-ethoxy)-phenyl]-methanone was accessible by lyophilization.

Preparation Procedure 0.50 g of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone were dissolved in 50 g of ethanol at 65° C. While spinning (rotary evaporator) at 40° C. maximum vacuum was applied. After complete evaporation of the solvent, the solid was further dried at ca. 25° C./5-20 mbar for 18 h. Analysis revealed amorphous [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

Solid State Properties of the Amorphous Form

XRPD-pattern, IR-spectrum, DSC curve, and TG curve and moisture sorption/desorption isotherms of the amorphous form are listed in FIGS. 13 to 17.

Example 5

Preparation of a Methylparaben Cocrystal Form

General

Cocrystals of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and methylparaben can be produced by digestion in solvents as e.g. ethanol and water. It can also be prepared by recrystallization of form A, B, C or amorphous form of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and methylparaben with or without seeding in solvent systems comprising but not limited to ethanol. The [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone-methylparaben ratio can range from 1:1 to 1:10.

Preparation Procedure 100 mg of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and 28 mg methylparaben (1 part [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone +1 part methylparaben) were dissolved in 0.3 mL ethanol and heated up to dissolve both substances. The clear solution was cooled down to room temperature without stirring. After 7 weeks the crystals were filtered, washed with ethanol/water (60/40 w/w) and dried at room temperature/0-20 mbar for 14 h.

Solid State Properties of the Methylparaben Cocrystal Form

XRPD-pattern, IR-spectrum, DSC curve, and TG curve of the methylparaben cocrystal are listed in FIGS. 18 to 21.

The invention claimed is:

1. A crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by at least three peaks selected from the following X-ray diffraction peaks obtained with a CuKα radiation, expressed in degrees 2Theta=13.1, 14.3, 15.4, 16.2, 17.1, 17.2, 17.6, 18.0, 19.8, 20.1, 20.4, 21.0, 22.6 and 24.3 (±0.2).

2. A crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by the following X-ray diffraction peaks obtained with a CuKα radiation, expressed in degrees 2Theta=13.1, 14.3, 15.4, 16.2, 17.1, 17.2, 17.6, 18.0, 19.8, 20.1, 20.4, 21.0, 22.6 and 24.3 (±0.2).

3. A crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by the X-ray diffraction pattern as substantially shown in FIG. 1.

4. A crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by an infrared spectrum having sharp bands at 3032, 1645, 1623, 1600, 1581, 1501, 1342, 1331, 1314, 1291, 1266, 1245, 1154, 1130, 1088, 1054, 1012, 976, 951, 922, 889, 824, 787, 758, 739, 714 and 636 cm$^{-1}$ (±3 cm$^{-1}$).

5. A crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by an infrared spectrum as substantially shown on FIG. 2.

6. A crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by at least three peaks selected from the following X-ray diffraction peaks obtained with a CuKα radiation, expressed in degrees 2Theta=11.4, 15.4, 16.2, 16.4, 17.8, 18.3, 19.2, 20.1, 21.0, 22.0, 22.5, 26.4 (±0.2).

7. A crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by the following X-ray diffraction peaks obtained with a CuKα radiation, expressed in degrees 2Theta=11.4, 15.4, 16.2, 16.4, 17.8, 18.3, 19.2, 20.1, 21.0, 22.0, 22.5 and 26.4 (±0.2).

8. A crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by the X-ray diffraction pattern as substantially shown in FIG. 5.

9. A crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by an infrared spectrum having sharp bands at 1644, 1635, 1621, 1599, 1567, 1514, 1488, 1398, 1343, 1328, 1291, 1266, 1183, 1155, 1090, 1022, 1003, 973, 958, 938, 920, 897, 822, 783, 753, 740, 683 and, 638 cm$^{-1}$ (±3 cm$^{-1}$).

10. A crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone characterized by an infrared spectrum as substantially shown in FIG. 6.

11. A method for preparing a crystalline form A of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprising recrystallization in a solvent selected from the group consisting of methanol, ethanol, 2-propanol, toluene, dioxane, ethanol/water, methanol/water, comprising:
  either recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone after seeding with form A;
  or recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and spontaneous crystallization below about 40° C., without seeding.

12. A method for preparing a crystalline form B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone comprising:
  either seeding an ethanol solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone with form B;
  or crystallization of an ethanol solution of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone without seeding;
  or recrystallization of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone in one or more solvents selected form the group consisting of methanol, ethanol, 1,4-dioxane and water mixtures thereof and seeding with form B.

13. A pharmaceutical composition comprising a crystalline form A or B of [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone as an active ingredient and a pharmaceutically acceptable carrier.

* * * * *